(12) United States Patent
Dalton et al.

(10) Patent No.: US 8,445,534 B2
(45) Date of Patent: May 21, 2013

(54) TREATING ANDROGEN DECLINE IN AGING MALE (ADAM)-ASSOCIATED CONDITIONS WITH SARMS

(75) Inventors: James T. Dalton, Lakeland, TN (US); Duane D. Miller, Germantown, TN (US); Donghua Yin, Paweatuck, CT (US); Yali He, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 247 days.

(21) Appl. No.: 12/632,619

(22) Filed: Dec. 7, 2009

(65) Prior Publication Data

US 2010/0137430 A1      Jun. 3, 2010

Related U.S. Application Data

(63) Continuation-in-part of application No. 10/849,039, filed on May 20, 2004, now abandoned, which is a continuation-in-part of application No. 10/270,233, filed on Oct. 15, 2002, now abandoned, which is a continuation-in-part of application No. 09/935,044, filed on Aug. 23, 2001, now Pat. No. 6,492,554, and a continuation-in-part of application No. 09/935,045, filed on Aug. 23, 2001, now Pat. No. 6,569,896, which is a continuation-in-part of application No. 09/644,970, filed on Aug. 24, 2000, now abandoned.

(60) Provisional application No. 60/300,083, filed on Jun. 25, 2001.

(51) Int. Cl.
    *A61K 31/275*   (2006.01)

(52) U.S. Cl.
    USPC ............ 514/522; 514/524; 514/616; 514/628

(58) Field of Classification Search
    USPC ................. 558/413, 414; 564/162; 514/522, 514/524, 616, 628
    See application file for complete search history.

(56) References Cited

U.S. PATENT DOCUMENTS

| | | | |
|---|---|---|---|
| 3,875,229 A | 4/1975 | Gold et al. | |
| 4,139,638 A | 2/1979 | Neri et al. | |
| 4,191,775 A | 3/1980 | Glen et al. | |
| 4,239,776 A | 12/1980 | Glen et al. | |
| 4,282,218 A | 8/1981 | Glen et al. | |
| 4,386,080 A | 5/1983 | Crossley et al. | |
| 4,465,507 A | 8/1984 | Konno et al. | |
| 4,636,505 A | 1/1987 | Tucker et al. | |
| 4,880,839 A | 11/1989 | Tucker et al. | |
| 5,162,504 A | 11/1992 | Horoszewicz et al. | |
| 5,609,849 A | 3/1997 | Kung et al. | |
| 5,656,651 A | 8/1997 | Sovak et al. | |
| 6,019,957 A | 2/2000 | Miller et al. | |
| 6,071,957 A | 6/2000 | Miller et al. | |
| 6,160,011 A * | 12/2000 | Miller et al. | 514/522 |
| 6,492,554 B2 | 7/2002 | Dalton et al. | |
| 6,569,896 B2 | 7/2002 | Dalton et al. | |
| 6,482,861 B2 | 11/2002 | Miller et al. | |
| 6,569,892 B2 | 5/2003 | Dalton et al. | |
| 6,838,484 B2 | 1/2005 | Steiner et al. | |
| 6,995,284 B2 | 2/2006 | Dalton et al. | |
| 6,998,500 B2 | 2/2006 | Dalton et al. | |
| 7,026,500 B2 | 4/2006 | Dalton et al. | |
| 7,595,402 B2 | 9/2009 | Miller et al. | |
| 7,759,520 B2 | 7/2010 | Dalton et al. | |
| 2001/0012839 A1 | 8/2001 | Miller et al. | |
| 2004/0014975 A1 | 1/2004 | Dalton et al. | |
| 2004/0029913 A1 | 2/2004 | Dalton et al. | |
| 2004/0260092 A1 | 12/2004 | Miller et al. | |
| 2005/0137172 A1 | 6/2005 | Dalton et al. | |

FOREIGN PATENT DOCUMENTS

| | | |
|---|---|---|
| CA | 2420279 | 2/2002 |
| EA | 200400774 | 12/2002 |
| EA | 200401043 | 2/2003 |
| EP | 0 040 932 | 2/1981 |
| EP | 0 100 172 | 2/1984 |
| EP | 000 2892 | 2/1985 |
| EP | 00198352 | 1/1989 |
| EP | 0253 503 | 12/1991 |
| EP | 1401801 | 11/2006 |
| GB | 1360001 | 3/1970 |
| JP | 52-128329 | 10/1977 |
| JP | 54-63047 | 12/1980 |
| WO | WO 95/19770 | 7/1995 |
| WO | WO 98 05962 | 2/1998 |
| WO | WO 98/53826 | * 12/1998 |

(Continued)

OTHER PUBLICATIONS

West, Anthony R., Solid State Chemistry and its Applications, Wiley, New York, 1988, pp. 358 & 365.*
Bernard Testa "Predicting drug metabolism: Concepts and challenges" Pure and Applied Chemistry 2004, vol. 76, No. 5, pp. 907-914.*
U.S. Appl. No. 09/935,044, filed Aug. 23, 2001, Dalton et al.
U.S. Appl. No. 09/935,045, filed Aug. 23, 2001, Dalton et al.
U.S. Appl. No. 09/644,970, filed Aug. 2, 2000, Dalton et al.
U.S. Appl. No. 10/298,229, filed Nov. 28, 2002, Miller et al.
U.S. Appl. No. 10/270,232, filed Oct. 15, 2002, Dalton et al.
U.S. Appl. No. 10/277,108, filed Oct. 23, 2002, Dalton et al.
U.S. Appl. No. 10/270,233, filed Oct. 15, 2002, Dalton et al.
U.S. Appl. No. 10/270,732, filed Oct. 15, 2002, Dalton et al.
U.S. Appl. No. 10/371,155, filed Feb. 24, 2003, Dalton et al.

(Continued)

*Primary Examiner* — Shailendra Kumar
(74) *Attorney, Agent, or Firm* — Pearl Cohen Zedek Latzer, LLP; Mark S. Cohen

(57) ABSTRACT

This invention provides methods for treatment and inhibition of a male subject having an Androgen Decline in Aging Male (ADAM)-associated condition, for example sexual dysfunction, decreased sexual libido, erectile dysfunction, hypogonadism, sarcopenia, osteopenia, osteoporosis, an alteration in cognition and mood, depression, anemia, hair loss, obesity, muscle loss, dry eye, memory loss, benign prostate hyperplasia and/or prostate cancer, by administering to the subject a selective androgen receptor modulator (SARM) compound and/or its analog, derivative, isomer, metabolite, pharmaceutically acceptable salt, pharmaceutical product, hydrate, N-oxide, pro-drug, polymorph, crystal, or any combination thereof.

20 Claims, 19 Drawing Sheets

FOREIGN PATENT DOCUMENTS

| | | |
|---|---|---|
| WO | WO 98/55153 | 12/1998 |
| WO | WO 01 27622 | 4/2001 |
| WO | WO 01 28990 | 4/2001 |
| WO | WO 01 34563 | 5/2001 |
| WO | WO 02 00617 | 1/2002 |
| WO | WO 02/16310 | 2/2002 |
| WO | WO 03/011302 | 2/2003 |
| WO | WO 03/049675 | 6/2003 |
| WO | WO 03/065992 | 8/2003 |
| WO | WO 03/074449 | 9/2003 |
| WO | WO 03/106401 | 12/2003 |
| WO | WO 2004/034978 | 4/2004 |
| WO | WO 2004/035736 | 4/2004 |
| WO | WO 2004/035738 | 4/2004 |
| WO | WO 2004/035739 | 4/2004 |
| WO | WO 2004/064747 | 8/2004 |
| WO | WO 2005/000794 | 1/2005 |
| WO | WO 2005/060647 | 7/2005 |

OTHER PUBLICATIONS

U.S. Appl. No. 10/371,209, filed Feb. 24, 2003, Dalton et al.
U.S. Appl. No. 10/371,211, filed Feb. 24, 2003, Dalton et al.
U.S. Appl. No. 10/371,210, filed Feb. 24, 2003, Dalton et al.
U.S. Appl. No. 10/359,270, filed Feb. 6, 2003, Steiner et al.
U.S. Appl. No. 10/310,150, filed Dec. 5, 2002, Steiner, et al.
Tucker and Glynne J. Chesterson, J. Med Chem. 1988, 31, pp. 885-887, "Resolution of the Nonsteroidal Antiandrogen—4'-Cyano-3-[(4-fluorophenyl)sulfonyl]-2-hydroxy-2-methyl-3'-(trifluoromethyl)-propionanilide and the Determination of the Absolute Configuration of the Active Enantiomer".
D. McKillop, et al., "Enantioselective metabolism and pharmacokinetics of Casodex in the male rat", Xenobiotica, 1995, vol. 25, No. 6, 623-634.
Leonid Kirkovsky, et al., "[$^{125}$I]-Radionated Bicalutamide Analogs as Potential Imaging Agents for Prostate Cancer", Poster Presentation MEDI 155, 214th ACS National Meeting, Las Vegas, NV, Sep. 7-11, 1997, Department of Pharmaceutical Sciences, University of Tennessee, Memphis, TN 38163.
David T. Baird and Anna F. Glasier, "Hormonal Contraception—Drug Therapy", The New England Journal of Medicine, May 27, 1993, pp. 1543-1549.
F.C. W. Wu, "Male Contraception: Current Status and Future Prospects", Clinical Endocrinology, (1988), 29, pp. 443-465.
World Health Organisation Task Force on Methods for the Regulation of Male Fertility, "Contraceptive efficacy of testosterone-induced azoospermia in normal men", The Lancet, vol. 336, Oct. 20, 1990, pp. 955-959 and 1517-1518.
C. G. Francisco, et al., "Long-acting contraceptive agents: testosterone esters of unsaturated acids", Steroids, Jan. 1990, vol. 55, Butterworths.
John M. Hoberman and Charles E. Yesalis, "The History of Synthetic Testosterone", Scientific American, Feb. 1995, pp. 76-81.
Leonid Kirkovsky, et al., "Approaches to Irreversible non-steroidal chiral antiandrogens", Department of Pharmaceutical Sciences, University of Tennessee, 47th Southeast/51st Southwest Joint Regional Meeting of the American Chemical Society, Memphis, TN, Nov. 29-Dec. 1, 1995.
David J. Handelsman, "Bridging the gender gap in contraception: another hurdle cleared" The Medical Journal of Australia, vol. 154, Feb. 18, 1996, pp. 230-233.
Edwards JP, Higuchi RI, Winn DT, Pooley CLF, Caferro TR, Hamann LG, Zhi L, Marschke KB, Goldman ME, and Jones TK. "Nonsteroidal androgen receptor agonists based on 4-(trifluoromethyl)-2H-pyrano [3, 2-g] quinolin-2-one", Bioorg. Med. Chem. Lett., 9: 1003, 1999.
Zhi L, Tegley CM, Marschke KB, and Jones TK. Switching androgen receptor antagonists to agonists by modifying C-ring substituents on piperidino[3,2-g]quinolone. Bioorg. Med. Chem. Lett., 9: 1009, 1999.
Higuchi RI, Edwards JP, Caferro TR, Ringgenberg JD, Kong JW, Hamann LG, Arienti KL, Marschke KB, Davis RL, Farmer LJ, and Jones TK. 4-Alkyl- and 3,4-diaklyl-1,2,3,4-tetrahydro-8-pyridono[5,6-g]quinolines: potent, nonsteroidal androgen receptor agonists. Bioorg. Med. Chem. Lett., 9:1335, 1999.
Hamann LG, Mani NS, Davis RL, Wang XN, Marschke KB, and Jones TK. Discovery of a potent, orally active nonsteroidal androgen receptor agonist: 4-ethyl-1,2,3,4-tetrahydro-6-(trifluoromethyl)-8-pyridono[5,6-g]-quinoline (LG121071). J. Med. Chem., 42: 210, 1999.
Rosen J, Day A, Jones TK, Jones ET, Nadzan AM, and Stein RB. Intracellular receptors and signal transducers and activators of transcription superfamilies: novel targets for small-molecule drug discovery. J. Med. Chem., 38: 4855, 1995.
Dalton JT, Mukherjee A, Zhu Z, Kirkovsky L, and Miller DD. Discovery of Nonsteroidal Androgens. Biochem. Biophys. Res. Commun., 244(1):1-4, 1998.
Edwards JP, West SJ, Pooley CLF, Marschke KB, Farmer LJ, and Jones TK. New nonsteroidal androgen receptor modulators based on 4-(trifluoromethyl)-2-(1H)-Pyrololidino[3,2-g]quinolone. Bioorg. Med. Chem. Lett., 8: 745, 1998.
Dalton JT, et al "Pharmacokinetics of Aminolevulinic Acid after Oral and Intravenous Dosing in Dogs." Drug Metabolism and Disposition, 27 (4):432-435, 1999.
Yin D, et al "Key Structural Features of Nonsteroidal Ligands for Binding and Activation of the Androgen Receptor." Molecular Pharmacology, 63:211-223, 2003.
Yin D, et al "Pharmacology, Pharmacokinetics and Metabolism of Acetothiolutamide, A Novel Nonsteroidal Agonist for the Androgen Receptor." Journal of Pharmacology and Experimental Therapeutics, 304(3):1323-1333, 2003.
Yin D, et al "Pharmacodynamics of Selective Androgen Receptor Modulators." Journal of Pharmacology and Experimental Therapeutics, 304(3):1334-1340, 2003.
Gao, W., et al "Comparison of the Pharmacological Effects of a Novel Selective Androgen Receptor Modulator (SARM), the 5{alpha}-Reductase Inhibitor Finasteride, and the Antiandrogen Hydroxyflutamide in Intact Rats: New Approach for Benign Prostate Hyperplasia (BPH)." Endocrinology, 145(12): 5420-5428, 2004.
Chen J, et al "A Selective Androgen Receptor Modulator (SARM) for Hormonal Male Contraception." Journal of Pharmacology and Experimental Therapeutics, 312(2): 546-553, 2005.
Bohl CE, et al "Structural Basis for Antagonism and Resistance of Bicalutamide in Prostate Cancer." Proc Natl Acad Sci USA. 102(17): 6201-6206, 2005.
Eliason et al., "High Throughput Fluorescence Polarization-Based Screening Assays for the Identification of Novel Nuclear Receptor Ligands," Abstracts of Papers, 223rd ACS National Meeting, Orlando, FL, United States, (2002), Apr. 7, 2002.
Berger et al., "Concepts and limitations in the application of radiolabeled antiandrogens, estrogens, or androgens as isotropic scanning agents for the prostate", Invest. Urol, (1975), 1391, 10-16.
Terashima, et al (1979) "Asymmetric Halolactonsation Reaction-1" Tetrahedron Letters vol. 35 2337-2343.
Corey (1987) "Asymmetric Bromolactonization Reaction: Synthesis of Optically Active 2-hydroxy-2-Methylalkanoic Acids from 2-Methylalkanoic Acids" Tetrahedron Letters vol. 28, No. 25 2801-2804.
Kirkovsky L, Mukherjee A, Yin D, Dalton JT, and Miller DD. Chiral Nonsteroidal Affinity Ligands for the Androgen Receptor. 1. Bicalutamide Analogs bearing Electrophilic Groups at the Aromatic Ring B. Journal of Medicinal Chemistry, 43: 581-590, 2000.
Matsumoto, "Hormonal therapy of male hypogonadism." Endocrinol. Met. Clin. N. Am. 23:857-75 (1994).
Zhou, et al., "Specificity of ligand-dependent androgen receptor stabilization: receptor domain interactions influence ligand dissociation and receptor stability." Molec. Endocrinol. 9:208-18 (1995).
Sundaram et al., "7 Alpha-Methyl-Nortestosterone(MENT): The Optimal Androgen for Male Contraception," Ann. Med., 25:199-205 (1993) ("Sundaram").
Steinberger et al., Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977).

Wu, "Effects of Testosterone Enanthate in Normal Men: Experience From a Multicenter Contraceptive Efficacy Study," Fertility and Sterility 65:626-36 (1996).

Tucker et al "Nonsteroidal antiandrogens. Synthesis and structure-activity relationships of 3-substituted derivatives of 2-hydroxypropionanilides." J. Med Chem (1988), 31, 954-959.

Buchwald et al. "Long-term, continuous intravenous heparin administration by an implantable infusion pump in ambulatory patients with recurrent venous thrombosis."Surgery 88:507 (1980).

Saudek et al."A preliminary trial of the programmable implantable medication system for insulin delivery." N. Engl. J. Med. 321:574 (1989).

Antonio J et al, "Effects of castration and androgen treatment on androgen-receptor levels in rat skeletal muscles," J Appl Physiol 87: 2016-2019, 1999.

Almeida SA et al, " Decreased spermatogenic and androgenic testicular functions in adult rats submitted to immobilization-induced stress from prepuberty" Braz. J. Med. Biol. Res. 31(11): 1443-8, Nov. 1998.

Lemus AE et al, "5alpha-reduction of norethisterone enhances its binding affinity for androgen receptors but diminishes its androgenic potency" J. Steroid. Biochem. Mol. Biol. 60(1-2): 121-9, Jan. 1997.

Langer, "New methods of drug delivery", Science 249:1527-1533 (1990).

Treat et al., in Liposomes in the Therapy of Infectious Disease and Cancer, Lopez-Berestein and Fidler (eds.), Liss, New York, pp. 353-365 (1989).

Lopez-Berestein, "Treatment of systematic fungal infections with liposomal-amphotericin B", pp. 317-327, 1989.

Sefton, "Implantable pumps", CRC Crit. Ref. Biomed. Eng. 14:201 (1987).

Goodson, in Medical Applications of Controlled Release, supra, vol. 2, pp. 115-138 (1984).

Abuchowski et al. "Immunosuppressive properties and circulating life of Achromobacter glutaminase-asparaginase covalently attached to polyethylene glycol in man" Cancer Treat Rep. 65(11-12): 1077-81 1981.

Katre et al. "Chemical modification of recombinant interleukin 2 by polyethylene glycol increases its potency in the murine Meth A sarcoma model" Proc Natl Acad Sci USA. 84(6):1487-91. Mar. 1987.

Wright C et al, "Analysis of myosin heavy chain mRNA expression by RT-PCR", J. Appl. Physiol. Oct. 1997 83(4): 1389-96.

Adams GR et al, Time course of myosin heavy chain transitions in neonatal rats: importance of innervation and thyroid state, Am J Physiol. 1999 Apr; 276(4 Pt 2): R954-61.

Allan, "Induction of a novel conformation in the progesterone receptor by ZK299 involves a defined region of the carboxyl-terminal tail", Mol Endocrinol. Oct. 1996;10(10):1206-13.

Dukes, "Nonsteroidal progestins and antiprogestins related to flutamide",Steroids. Oct.-Nov. 2000;65(10-11):725-31.

Mukherjee et al., "Affinity labeling of the androgen receptor with nonsteroidal chemoaffinity ligands", Biochem. Pharmacol. vol. 58, pp. 1259-1267, 1999.

* cited by examiner

TREATING ANDROGEN DECLINE IN AGING MALE (ADAM)-ASSOCIATED CONDITIONS WITH SARMS

CROSS REFERENCE TO RELATED APPLICATIONS

This application is a Continuation-in-Part of U.S. Ser. No. 10/849,039, filed May 20, 2004, now abandoned, which is a Continuation-in-Part Application of U.S. Ser. No. 10/270,233, filed Oct. 15, 2002, now abandoned, which is a Continuation-in-Part Application of U.S. Ser. No. 09/935,044, filed Aug. 23, 2001, now U.S. Pat. No. 6,492,554, and of U.S. Ser. No. 09/935,045, filed Aug. 23, 2001, now U.S. Pat. No. 6,569,896, which are Continuation-in-Part Applications of U.S. Ser. No. 09/644,970 filed Aug. 24, 2000 now abandoned; and claims priority of U.S. Ser. No. 60/300,083, filed Jun. 25, 2001, which are hereby incorporated in their entirety herein by reference.

FIELD OF THE INVENTION

The present invention relates to a novel class of androgen receptor targeting agents (ARTA), which demonstrate androgenic and anabolic activity of a nonsteroidal ligand for the androgen receptor. The agents define a new subclass of compounds, which are selective androgen receptor modulators (SARMs) useful for a) male contraception; b) treatment of a variety of hormone-related conditions, for example conditions associated with Androgen Decline in Aging Male (ADAM); c) treatment of conditions associated with Androgen Decline in Female (ADIF); d) treatment and/or prevention of chronic muscular wasting; and/or e) decreasing the incidence of, halting or causing a regression of prostate cancer.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199-205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320- 28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821-29 (1996)).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626-36 (1996)).

Steroidal ligands which bind the AR and act as androgens (e.g. testosterone enanthate) or as antiandrogens (e.g. cyproterone acetate) have been known for many years and are used clinically (Wu 1988). Although nonsteroidal antiandrogens are in clinical use for hormone-dependent prostate cancer, nonsteroidal androgens have not been reported. For this reason, research on male contraceptives has focused solely on steroidal compounds.

Prostate cancer is one of the most frequently occurring cancers among men in the United States, with hundreds of thousands of new cases diagnosed each year. Unfortunately, over sixty percent of newly diagnosed cases of prostate cancer are found to be pathologically advanced, with no cure and a dismal prognosis. One approach to this problem is to find prostate cancer earlier through screening programs and thereby reduce the number of advanced prostate cancer patients. Another strategy, however, is to develop drugs to prevent prostate cancer. One third of all men over 50 years of age have a latent form of prostate cancer that may be activated into the life-threatening clinical prostate cancer form. The frequency of latent prostatic tumors has been shown to increase substantially with each decade of life from the 50s (5.3-14%) to the 90s (40-80%). The number of people with latent prostate cancer is the same across all cultures, ethnic groups, and races, yet the frequency of clinically aggressive cancer is markedly different. This suggests that environmental factors may play a role in activating latent prostate cancer. Thus, the development of treatment and preventative strategies against prostate cancer may have the greatest overall impact both medically and economically against prostate cancer.

Osteoporosis is a systemic skeletal diseaseor Characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex-hormones at maturity (direct decline in androgens as well as lower levels of estrogens derived from peripheral aromatization of androgens) is associated with the frailty of bones. This effect is also observed in males who have been castrated.

Androgen decline in the aging male (ADAM) refers to a progressive decrease in androgen production, common in males after middle age. The syndrome is characterized by alterations in the physical and intellectual domains that correlate with and can be corrected by manipulation of the androgen milieu. ADAM is characterized biochemically by a decrease not only in serum androgen, but also in other hormones, such as growth hormone, melatonin and dehydroepiandrosterone. Clinical manifestations include fatigue, depression, decreased libido, sexual dysfunction, erectile dysfunction, hypogonadism, osteoporosis, hair loss, obesity, sarcopenia, osteopenia, benign prostate hyperplasia, and alterations in mood and cognition.

Androgen Deficiency in Female (ADIF) refers to a variety of hormone-related conditions including, common in females after middle agest. The syndrome is characterized by sexual dysfunction, decreased sexual libido, hypogonadism, sarcopenia, osteopenia, osteoporosis, alterations in cognition and mood, anemia, depression, anemia, hair loss, obesity, endometriosis, breast cancer, uterine cancer and ovarian cancer.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle. The loss of muscle mass that occurs during muscle wasting can be characterized by a muscle protein breakdown or degradation. Protein degradation occurs because of an unusually high rate of protein degradation, an unusually low rate of protein synthesis, or a combination of both. Protein degradation, whether caused by a high degree of protein degradation or a low degree of protein synthesis, leads to a decrease in muscle mass and to muscle wasting. Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Diseaseor CHronic Obstructive Pulmonary Disease (COPD), Cancer, end stage Renal failure, Emphysema, Osteomalacia, HIV Infection, AIDS, and Cardiomyopathy, In addition, other circumstances and conditions are linked to and can cause muscle wasting. These include chronic lower back pain, advanced age, central nervous system (CNS) injury, peripheral nerve injury, spinal cord injury or Chemical injury, central nervous system (CNS) damage, peripheral nerve damage, spinal cord damage or CHemical damage, burns, disuse deconditioning that occurs when a limb is immobilized, long term hospitalization due to illness or injury, and alcoholism. Muscle wasting, if left unabated, can have dire health consequences. For example, the changes that occur during muscle wasting can lead to a weakened physical state that is detrimental to an individual's health, resulting in increased susceptibility to infection, poor performance status and susceptibility to injury.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, benign prostate hyperplasia, alterations in mood and cognition and prostate cancer; c) treatment of conditions associated with ADIF, such as sexual dysfunction, decreased sexual libido, hypogonadism, sarcopenia, osteopenia, osteoporosis, alterations in cognition and mood, depression, anemia, hair loss, obesity, endometriosis, breast cancer, uterine cancer and ovarian cancer; d) treatment and/or prevention of acute and/or chronic muscular wasting conditions; e) preventing and/or treating dry eye conditions; f) oral androgen replacement therapy; and/or g) decreasing the incidence of, halting or causing a regression of prostate cancer.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 7: Effect of testosterone proprionate and Compound 1 on myosin heavy chain (MHC) IIb mRNA expression.

Figure 1:
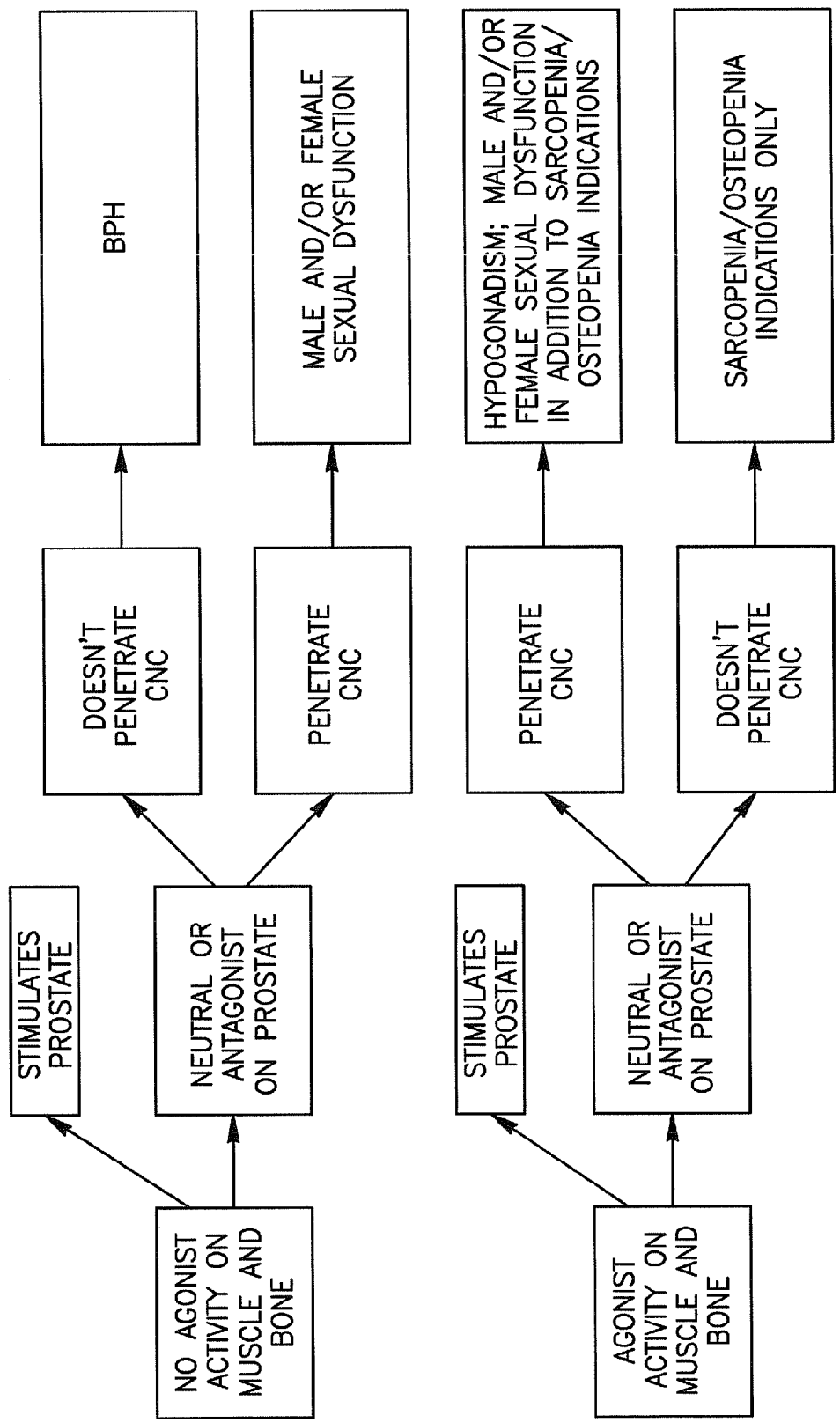
FIG. 1: Flowchart of ADAM-associated conditions.
Figure 2:
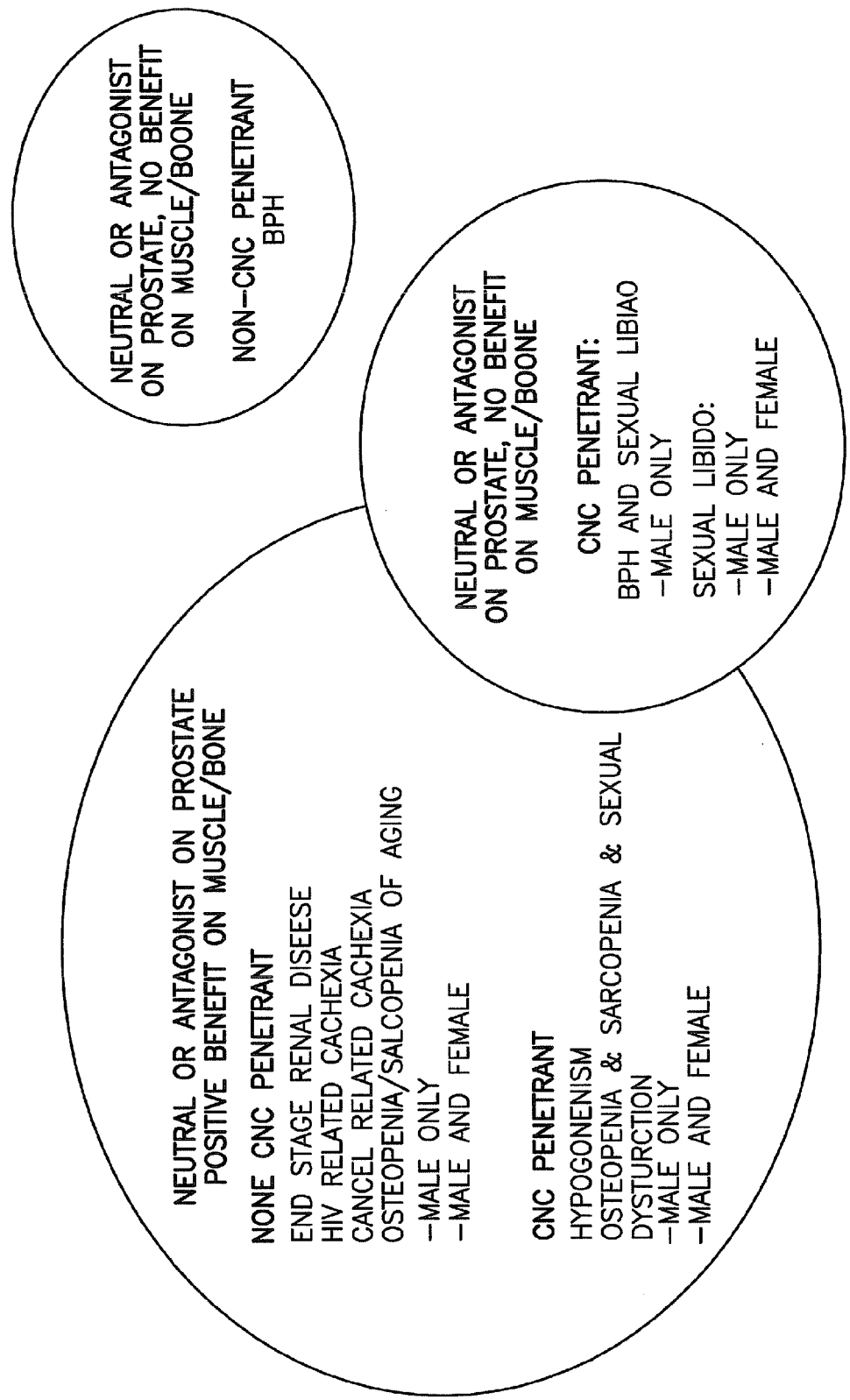
FIG. 2: Schematic illustration of ADAM-associated conditions.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

The present invention provides methods of treating, suppressing, inhibiting or reducing the incidence of an ADAM-associated condition in a male subject, by administering to the subject a SARM compound and/or its analog, derivative, isomer, metabolite, pharmaceutically acceptable salt, pharmaceutical product, hydrate, N-oxide, pro-drug, polymorph, crystal, or any combination thereof. The present invention further provides methods of treating, preventing, suppressing, inhibiting or reducing the incidence of sexual dysfunction, decreased sexual libido, erectile dysfunction, hypogonadism, sarcopenia, osteopenia, osteoporosis, an alteration in cognition and mood, depression, anemia, hair loss, obesity, muscle loss, BPH, dry eye, memory loss, and/or prostate cancer due to ADAM in a male subject, by administering to the subject a SARM compound and/or its analog, derivative, isomer, metabolite, pharmaceutically acceptable salt, pharmaceutical product, hydrate, N-oxide, pro-drug, polymorph, crystal, or any combination thereof.

Thus, in one embodiment, this invention relates to a method of treating a male subject suffering from an Androgen Decline in Aging Male (ADAM)-associated condition, comprising the step of administering to the subject a selective androgen receptor modulator (SARM) compound. In another embodiment, the method comprises administering an analog, derivative, isomer, metabolite, pharmaceutically acceptable salt, pharmaceutical product, hydrate or N-oxide, prodrug, polymorph or crystal of the SARM compound, or any combination thereof. In one embodiment, the male subject is an aging male subject.

In another embodiment, the present invention provides a method of preventing, suppressing, inhibiting or reducing the incidence of an ADAM- associated condition in a male subject, comprising the step of administering to the subject a selective androgen receptor modulator (SARM) compound. In another embodiment, the method comprises administering an analog, derivative, isomer, metabolite, pharmaceutically acceptable salt, pharmaceutical product, hydrate or N-oxide, prodrug, polymorph or crystal of the SARM compound, or any combination thereof. In one embodiment, the male subject is an aging male subject.

In another embodiment, the present invention provides a method of treating a male subject suffering from sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer due to Androgen Decline in an Aging Male (ADAM), comprising the step of administering to the subject a selective androgen receptor modulator (SARM) compound. In another embodiment, the method comprises administering an analog, derivative, isomer, metabolite, pharmaceutically acceptable salt, pharmaceutical product, hydrate or N-oxide, prodrug, polymorph or crystal of the SARM compound, or any combination thereof. In one embodiment, the male subject is an aging male subject.

In another embodiment, the present invention provides a method of preventing, suppressing, inhibiting or reducing the incidence of an ADAM-associated condition selected from sexual dysfunction, decreased sexual libido, erectile dysfunction, hypogonadism, sarcopenia, osteopenia, osteoporosis, alterations in cognition and mood, depression, anemia, hair loss, obesity, benign prostate hyperplasia and/or prostate cancer in a male subject, comprising the step of administering to the subject a selective androgen receptor modulator (SARM) compound. In another embodiment, the method comprises administering an analog, derivative, isomer, metabolite, pharmaceutically acceptable salt, pharmaceutical product, hydrate or N-oxide, prodrug, polymorph or crystal of the SARM compound, or any combination thereof. In one embodiment, the male subject is an aging male subject.

In one embodiment, the SARM compound that is effective at treating, preventing, suppressing, inhibiting or reducing the incidence of the ADAM-associated condition is a compound represented by the structure of formula I:

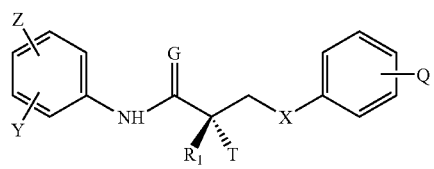

I wherein G is O or S;
X is a bond, O, $CH_2$, NH, Se, PR, NO or NR;
T is OH, OR, —$NHCOCH_3$, or NHCOR Z is $NO_2$, CN, COOH, COR, NHCOR or CONHR;
Y is $CF_3$, F, I, Br, Cl, CN, $C(R)_3$ or $Sn(R)_3$;
Q is alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, OCN; or
Q together with the benzene ring to which it is attached is a fused ring system represented by structure A, B or C:

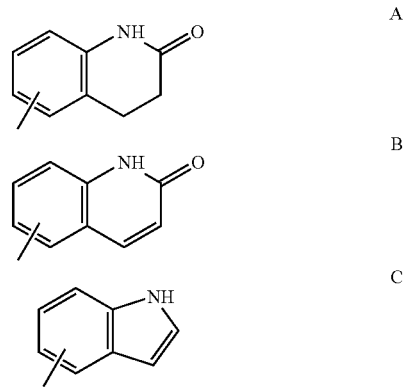

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and
$R_1$ is $CH_3$, $CH_2F$, $CHF_2$, $CF_3$, $CH_2CH_3$, or $CF_2CF_3$.

In one embodiment, the SARM is an analog of the compound of formula I. In another embodiment, the SARM is a derivative of the compound of formula I. In another embodiment, the SARM is an isomer of the compound of formula I. In another embodiment, the SARM is a metabolite of the compound of formula I. In another embodiment, the SARM is a pharmaceutically acceptable salt of the compound of formula I. In another embodiment, the SARM is a pharmaceutical product of the compound of formula I. In another embodiment, the SARM is a hydrate of the compound of formula I. In another embodiment, the SARM is an N-oxide of the compound of formula I. In another embodiment, the SARM is a crystal of the compound of formula I. In another embodiment, the SARM is a polymorph of the compound of formula I. In another embodiment, the SARM is a prodrug of the compound of formula I. In another embodiment, the SARM is a combination of any of an analog, derivative, metabolite, isomer, pharmaceutically acceptable salt, pharmaceutical product, hydrate, N-oxide, crystal, polymorph or prodrug of the compound of formula I.

In one embodiment, the SARM compound is a compound of formula I wherein X is O. In one embodiment, the SARM compound is a compound of formula I wherein G is O. In another embodiment, the SARM compound is a compound of formula I wherein Z is $NO_2$. In another embodiment, the SARM compound is a compound of formula I wherein Z is CN. In another embodiment, the SARM compound is a compound of formula I wherein Y is $CF_3$. In another embodiment, the SARM compound is a compound of formula I wherein Q is $NHCOCH_3$. In another embodiment, the SARM compound is a compound of formula I wherein Q is F. In another embodiment, the SARM compound is a compound of formula I wherein Q is halogen. In another embodiment, the SARM compound is a compound of formula I wherein X is O, Z is CN and Q is halogen. In another embodiment, the SARM compound is a compound of formula I wherein X is O, Z is CN and Q is F. In another embodiment, the SARM compound is a compound of formula I wherein T is OH. In another embodiment, the SARM compound is a compound of formula I wherein $R_1$ is $CH_3$.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituent Q can be in any position of the ring carrying this substituent (hereinafter "B ring"). In one embodiment, the substituent Q is in the para position of the B ring. In another embodiment, the substituent Q is $NHCOCH_3$ and is in the para position of the B ring. In another embodiment, the substituent Q is F and is in the para position of the B ring. In another embodiment, the substituent Q is halogen and is in the para position of the B ring.

In another embodiment, the SARM compound that is effective at treating, preventing, suppressing, inhibiting or reducing the incidence of the ADAM-associated condition is a compound represented by the structure of formula II:

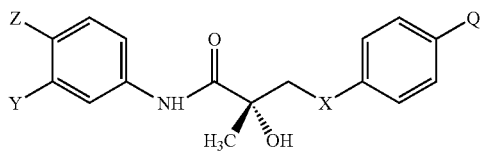

wherein X is a bond, O, $CH_2$, NH, Se, PR, NO or NR;
Z is $NO_2$, CN, COOH, COR, NHCOR or CONHR;
Y is $CF_3$, F, I, Br, Cl, CN, $C(R)_3$ or $Sn(R)_3$;
Q is alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO, OCN; or Q together with the benzene ring to which it is attached is a fused ring system represented by structure A, B or C:

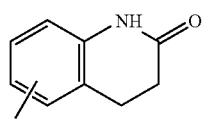

A

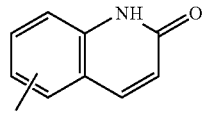

B

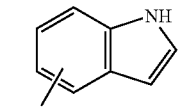

C

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH.

In one embodiment, the SARM is an analog of the compound of formula II. In another embodiment, the SARM is a derivative of the compound of formula II. In another embodiment, the SARM is an isomer of the compound of formula II. In another embodiment, the SARM is a metabolite of the compound of formula II. In another embodiment, the SARM is a pharmaceutically acceptable salt of the compound of formula II. In another embodiment, the SARM is a pharmaceutical product of the compound of formula II. In another embodiment, the SARM is a hydrate of the compound of formula II. In another embodiment, the SARM is an N-oxide of the compound of formula II. In another embodiment, the SARM is a crystal of the compound of formula II. In another embodiment, the SARM is a polymorph of the compound of formula II. In another embodiment, the SARM is a prodrug of the compound of formula II. In another embodiment, the SARM is a combination of any of an analog, derivative, metabolite, isomer, pharmaceutically acceptable salt, pharmaceutical product, hydrate, N-oxide, crystal, polymorph or prodrug of the compound of formula II.

In one embodiment, the SARM compound is a compound of formula II wherein X is O. In another embodiment, the SARM compound is a compound of formula II wherein Z is $NO_2$. In another embodiment, the SARM compound is a compound of formula II wherein Z is CN. In another embodiment, the SARM compound is a compound of formula II wherein Y is $CF_3$. In another embodiment, the SARM compound is a compound of formula II wherein Q is $NHCOCH_3$. In another embodiment, the SARM compound is a compound of formula II wherein Q is F. In another embodiment, the SARM compound is a compound of formula II wherein Q is halogen. In another embodiment, the SARM compound is a compound of formula II wherein X is O, Z is CN and Q is halogen. In another embodiment, the SARM compound is a compound of formula I wherein X is O, Z is CN and Q is F.

In another embodiment, the SARM compound that is effective at treating, preventing, suppressing, inhibiting or reducing the incidence of the ADAM-associated condition is a compound represented by the structure of formula III:

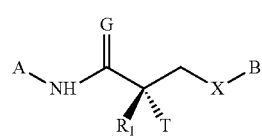

III wherein X is a bond, O, $CH_2$, NH, Se, PR, NO or NR;
G is O or S;
$R_1$ is $CH_3$, $CH_2F$, $CHF_2$, $CF_3$, $CH_2CH_3$, or $CF_2CF_3$;
T is OH, OR, —$NHCOCH_3$, or NHCOR;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
A is a ring selected from:

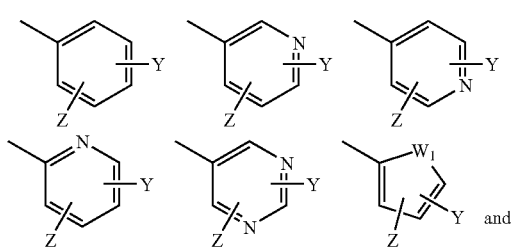

and

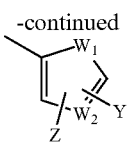

B is a ring selected from:

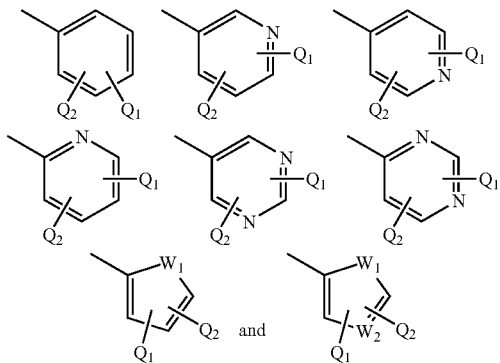

wherein A and B cannot simultaneously be a benzene ring;

Z is $NO_2$, CN, COOH, COR, NHCOR or CONHR;

Y is $CF_3$, F, I, Br, Cl, CN $CR_3$ or $SnR_3$;

$Q_1$ and $Q_2$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR, NCS, SCN, NCO, OCN,

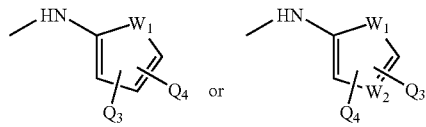

$Q_3$ and $Q_4$ are independently of each other a hydrogen, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$W_1$ is O, NH, NR, NO or S; and $W_2$ is N or NO.

In one embodiment, the SARM is an analog of the compound of formula III. In another embodiment, the SARM is a derivative of the compound of formula III. In another embodiment, the SARM is an isomer of the compound of formula III. In another embodiment, the SARM is a metabolite of the compound of formula III. In another embodiment, the SARM is a pharmaceutically acceptable salt of the compound of formula III. In another embodiment, the SARM is a pharmaceutical product of the compound of formula III. In another embodiment, the SARM is a hydrate of the compound of formula III. In another embodiment, the SARM is an N-oxide of the compound of formula III. In another embodiment, the SARM is a crystal of the compound of formula III. In another embodiment, the SARM is a polymorph of the compound of formula III. In another embodiment, the SARM is a prodrug of the compound of formula III. In another embodiment, the SARM is a combination of any of an analog, derivative, metabolite, isomer, pharmaceutically acceptable salt, pharmaceutical product, hydrate, N-oxide, crystal, polymorph or prodrug of the compound of formula III.

In one embodiment, the SARM compound is a compound of formula III wherein X is O. In another embodiment, the SARM compound is a compound of formula III wherein G is O. In another embodiment, the SARM compound is a compound of formula I wherein T is OH. In another embodiment, the SARM compound is a compound of formula III wherein $R_1$ is $CH_3$. In another embodiment, the SARM compound is a compound of formula III wherein Z is $NO_2$. In another embodiment, the SARM compound is a compound of formula III wherein Z is CN. In another embodiment, the SARM compound is a compound of formula III wherein Y is $CF_3$. In another embodiment, the SARM compound is a compound of formula III wherein $Q_1$ is $NHCOCH_3$. In another embodiment, the SARM compound is a compound of formula III wherein $Q_1$ is F. In another embodiment, the SARM compound is a compound of formula III wherein $Q_1$ is halogen. In another embodiment, the SARM compound is a compound of formula III wherein X is O, G is O, Z is CN and $Q_1$ is halogen. In another embodiment, the SARM compound is a compound of formula III wherein X is O, G is O, Z is CN and $Q_1$ is F.

The substituents Z and Y can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents $Q_1$ and $Q_2$ can be in any position of the ring carrying these substituents (hereinafter "B ring"). In one embodiment, the substitutent $Q_1$ is in the para position of the B ring. In another embodiment, the subsituent is $Q_2$ is H. In another embodiment, the substitutent $Q_1$ is in the para position of the B ring and the subsituent is $Q_2$ is H. In another embodiment, the substitutent $Q_1$ is $NHCOCH_3$ and is in the para position of the B ring, and the substituent is $Q_2$ is H. In another embodiment, the substitutent $Q_1$ is halogen and is in the para position of the B ring, and the substituent is $Q_2$ is H. In another embodiment, the substitutent $Q_1$ is F and is in the para position of the B ring, and the substituent is $Q_2$ is H.

In another embodiment, the SARM compound that is effective at treating, preventing, suppressing, inhibiting or reducing the incidence of the ADAM-associated condition is a compound represented by the structure of formula IV:

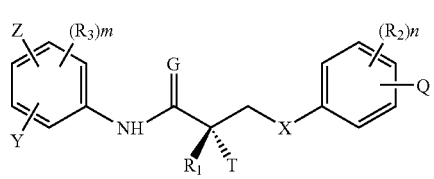

wherein X is a bond, O, $CH_2$, NH, Se, PR, NO or NR;

G is O or S;

T is OH, OR, —$NHCOCH_3$, or NHCOR;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$ or SR;

$R_3$ is H, F, Cl, Br, I, CN, $NO_2$, COR, COOH, CONHR, $CF_3$, $Sn(R)_3$, or $R_3$ together with the benzene ring to which it is attached forms a fused ring system represented by the structure:

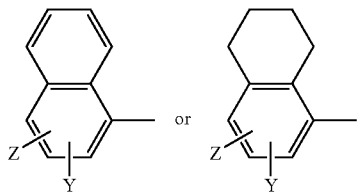

Z is $NO_2$, CN, COR, COOH, or CONHR;
Y is $CF_3$, F, Br, Cl, I, CN, or $Sn(R)_3$;
Q is H, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR, NCS, SCN, NCO, OCN; or Q together with the benzene ring to which it is attached is a fused ring system represented by structure A, B or C:

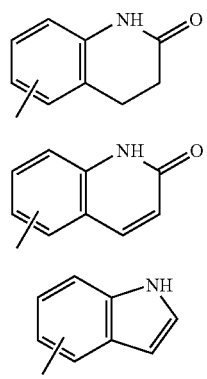

n is an integer of 1-4; and
m is an integer of 1-3.

In one embodiment, the SARM is an analog of the compound of formula IV. In another embodiment, the SARM is a derivative of the compound of formula IV. In another embodiment, the SARM is an isomer of the compound of formula IV. In another embodiment, the SARM is a metabolite of the compound of formula IV. In another embodiment, the SARM is a pharmaceutically acceptable salt of the compound of formula IV. In another embodiment, the SARM is a pharmaceutical product of the compound of formula IV. In another embodiment, the SARM is a hydrate of the compound of formula IV. In another embodiment, the SARM is an N-oxide of the compound of formula IV. In another embodiment, the SARM is a crystal of the compound of formula IV. In another embodiment, the SARM is a polymorph of the compound of formula IV. In another embodiment, the SARM is a prodrug of the compound of formula IV. In another embodiment, the SARM is a combination of any of an analog, derivative, metabolite, isomer, pharmaceutically acceptable salt, pharmaceutical product, hydrate, N-oxide, crystal, polymorph or prodrug of the compound of formula IV.

In one embodiment, the SARM compound is a compound of formula IV wherein X is O. In another embodiment, the SARM compound is a compound of formula IV wherein G is O. In another embodiment, the SARM compound is a compound of formula IV wherein Z is $NO_2$. In another embodiment, the SARM compound is a compound of formula IV wherein Z is CN. In another embodiment, the SARM compound is a compound of formula IV wherein Y is $CF_3$. In another embodiment, the SARM compound is a compound of formula IV wherein Q is $NHCOCH_3$. In another embodiment, the SARM compound is a compound of formula IV wherein Q is F. In another embodiment, the SARM compound is a compound of formula IV wherein T is OH. In another embodiment, the SARM compound is a compound of formula IV wherein $R_1$ is $CH_3$. In another embodiment, the SARM compound is a compound of formula IV wherein Q is F and $R_2$ is $CH_3$. In another embodiment, the SARM compound is a compound of formula IV wherein Q is F and $R_2$ is Cl. In another embodiment, the SARM compound is a compound of formula N wherein Q is halogen and $R_2$ is halogen. In another embodiment, the SARM compound is a compound of formula IV wherein Q is halogen and $R_2$ is halogen, Z is CN and $R_3$ is H. In another embodiment, the SARM compound is a compound of formula IV wherein $R_3$ is H.

The substituents Z, Y and $R_3$ can be in any position of the ring carrying these substituents (hereinafter "A ring"). In one embodiment, the substituent Z is in the para position of the A ring. In another embodiment, the substituent Y is in the meta position of the A ring. In another embodiment, the substituent Z is in the para position of the A ring and substituent Y is in the meta position of the A ring.

The substituents Q and $R_2$ can be in any position of the ring carrying these substituents (hereinafter "B ring"). In one embodiment, the substitutent Q is in the para position of the B ring. In another embodiment, the substitutent Q is in the para position of the B ring. In another embodiment, the substitutent Q is $NHCOCH_3$ and is in the para position of the B ring. In another embodiment, the substitutent Q is F and is in the para position of the B ring. In another embodiment, the substitutent Q is halogen and is in the para position of the B ring.

As contemplated herein, when the integers m and n are greater than one, the substituents $R_2$ and $R_3$ are not limited to one particular substituent, and can be any combination of the substituents listed above.

In another embodiment, the SARM compound that is effective at treating, preventing, suppressing, inhibiting or reducing the incidence of the ADAM-associated condition is a compound represented by the structure of formula V:

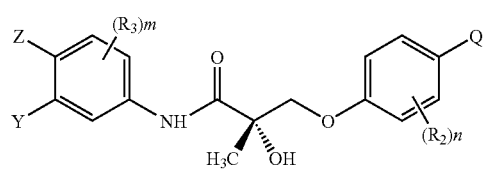

wherein
$R_2$ is F, Cl, Br, I, $CH_3$, $CF_3$, OH, CN, $NO_2$, $NHCOCH_3$, $NHCOCF_3$, NHCOR, alkyl, arylalkyl, OR, $NH_2$, NHR, $N(R)_2$ or SR;
$R_3$ is H, F, Cl, Br, I, CN, $NO_2$, COR, COOH, CONHR, $CF_3$, $Sn(R)_3$, or $R_3$ together with the benzene ring to which it is attached forms a fused ring system represented by the structure:

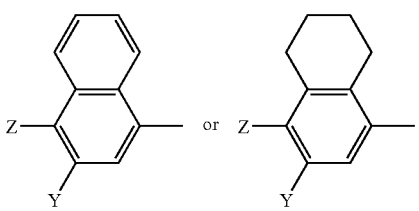

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

Z is $NO_2$, CN, COR, COOH, or CONHR;

Y is $CF_3$, F, Br, Cl, I, CN, or $Sn(R)_3$;

Q is H, alkyl, F, Cl, Br, I, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OH, OR, COR, OCOR, $OSO_2R$, $SO_2R$, SR, NCS, SCN, NCO, OCN; or Q together with the benzene ring to which it is attached is a fused ring system represented by structure A, B or C:

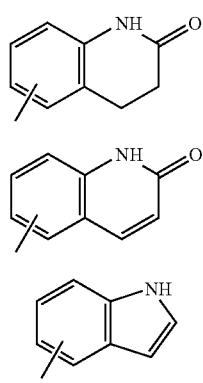

n is an integer of 1-4; and
m is an integer of 1-3.

In one embodiment, the SARM is an analog of the compound of formula V. In another embodiment, the SARM is a derivative of the compound of formula V. In another embodiment, the SARM is an isomer of the compound of formula V. In another embodiment, the SARM is a metabolite of the compound of formula V. In another embodiment, the SARM is a pharmaceutically acceptable salt of the compound of formula V. In another embodiment, the SARM is a pharmaceutical product of the compound of formula V. In another embodiment, the SARM is a hydrate of the compound of formula V. In another embodiment, the SARM is an N-oxide of the compound of formula V. In another embodiment, the SARM is a crystal of the compound of formula V. In another embodiment, the SARM is a polymorph of the compound of formula V. In another embodiment, the SARM is a prodrug of the compound of formula V. In another embodiment, the SARM is a combination of any of an analog, derivative, metabolite, isomer, pharmaceutically acceptable salt, pharmaceutical product, hydrate, N-oxide, crystal, polymorph or prodrug of the compound of formula V.

In another embodiment, the SARM is a compound of formula V wherein Z is $NO_2$. In another embodiment, the SARM is a compound of formula V wherein Z is CN. In another embodiment, the SARM is a compound of formula V wherein Y is $CF_3$. In another embodiment, the SARM is a compound of formula V wherein Q is $NHCOCH_3$. In another embodiment, the SARM is a compound of formula V wherein Q is F. In another embodiment, the SARM is a compound of formula V wherein Q is halogen. In another embodiment, the SARM is a compound of formula V wherein Q is F and $R_2$ is $CH_3$. In another embodiment, the SARM is a compound of formula V wherein Q is F and $R_2$ is Cl. In another embodiment, to the SARM is a compound of formula V wherein Q is halogen and $R_2$ is halogen. In another embodiment, the SARM compound is a compound of formula V wherein Q is halogen and $R_2$ is halogen, Z is CN and $R_3$ is H. In another embodiment, the SARM compound is a compound of formula V wherein $R_3$ is H.

The substituents Z, Y and $R_3$ can be in any position of the A ring, and the substituents Q and $R_2$ can be in any position of B ring, as discussed above for compound IV. Furthermore, as discussed above, when the integers m and n are greater than one, the substituents $R_2$ and $R_3$ are not limited to one particular substituent, and can be any combination of the substituents listed above.

In another embodiment, the SARM compound that is effective at treating, preventing, suppressing, inhibiting or reducing the incidence of the ADAM-associated condition is a compound represented by the structure of formula 1:

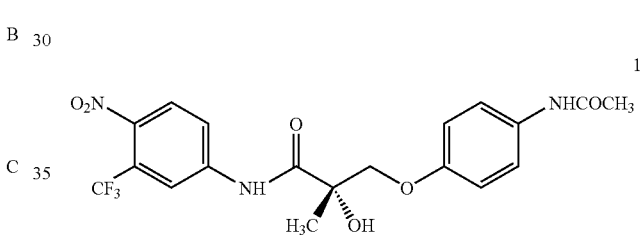

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 2:

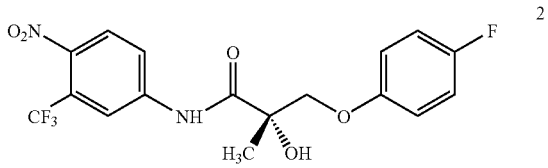 [SMILES: C[C@](O)(COc1ccc(F)cc1)C(=O)Nc1ccc([N+](=O)[O-])c(C(F)(F)F)c1]

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 3:

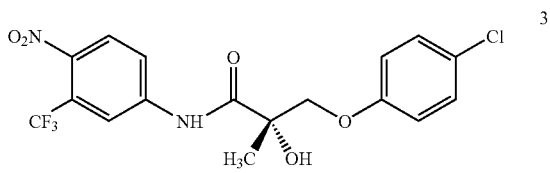 [SMILES: C[C@](O)(COc1ccc(Cl)cc1)C(=O)Nc1ccc([N+](=O)[O-])c(C(F)(F)F)c1]

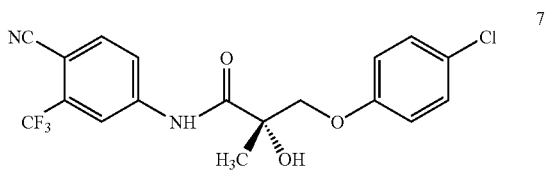

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 4:

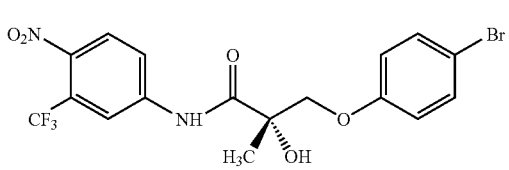

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 5:

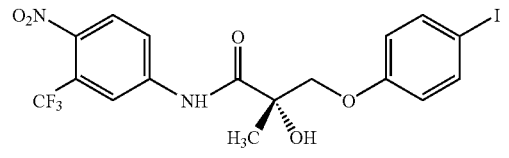

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 6:

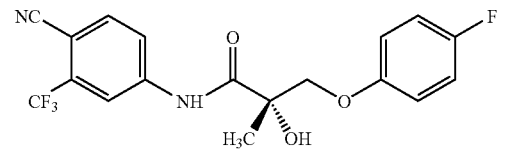 [SMILES: C[C@](O)(COc1ccc(F)cc1)C(=O)Nc1ccc(C#N)c(C(F)(F)F)c1]

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 7:

or its analog, derivative, isomer, metabolite, pharmaceutically acceptable salt, pharmaceutical product, hydrate or N-oxide, pro-drug, polymorph or crystal thereof.

In another embodiment, the SARM compound that is effective at treating, preventing, suppressing, inhibiting or reducing the incidence of the ADAM-associated condition is a compound represented by the structure of formula 8:

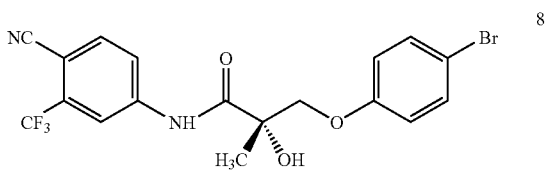 [SMILES: C[C@](O)(COc1ccc(F)cc1)C(=O)Nc1ccc(C#N)c(C(F)(F)F)c1]

or its analog, derivative, isomer, metabolite, pharmaceutically acceptable salt, pharmaceutical product, hydrate or N-oxide, pro-drug, polymorph or crystal thereof.

The substituent R is defined, in one embodiment, as an alkyl, haloalkyl, dihaloalkyl, trihaloalkyl, $CH_2F$, $CHF_2$, $CF_3$, $CF_2CF_3$; aryl, phenyl, F, Cl, Br, I, alkenyl, or hydroxyl (OH).

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen (e.g. F, Cl, Br, I), hydroxy, alkoxy carbonyl, amido, alkylamido, dialkylamido, nitro, amino, alkylamino, dialkylamino, carboxyl, thio and thioalkyl.

A "haloalkyl" group refers, in one embodiment, to an alkyl group as defined above, which is substituted by one or more halogen atoms, e.g. by F, Cl, Br or I. A "halogen" refers to elements of Group VII or the periodic table, e.g. F, Cl, Br or I.

An "aryl" group refers, in one embodiment, to an aromatic group having at least one carbocyclic aromatic group or heterocyclic aromatic group, which may be unsubstituted or substituted by one or more groups selected from halogen (e.g. F, Cl, Br, I), haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers, in one embodiment, to an OH group. An "alkenyl" group refers, in one embodiment, to a group having at least one carbon-carbon double bond.

An "arylalkyl" group refers, in one embodiment, to an alkyl bound to an aryl, wherein alkyl and aryl are as defined above. An example of an aralkyl group is a benzyl group.

As defined herein, the term "isomer" includes, but is not limited to, optical isomers and analogs, structural isomers and analogs, conformational isomers and analogs, and the like.

In another embodiment, this invention encompasses the use of various optical isomers of the SARM compounds. It will be appreciated by those skilled in the art that the SARM compounds of the present invention contain at least one chiral center. Accordingly, the SARM compounds used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of obesity and related disorders as described herein. In one embodiment, the SARM compounds are the pure (R)-isomers. In another embodiment, the SARM compounds are the pure (S)-isomers. In another embodiment, the SARM compounds are a mixture of the (R)- and the (S) isomers. In another embodiment, the SARM compounds are a racemic mixture comprising an equal amount of the (R)- and the (S) isomers. It is well known in the art how to prepare optically active forms (for example, by resolution of the racemic form by recrystallization techniques, by synthesis from optically-active starting materials, by chiral synthesis, or by chromatographic separation using a chiral stationary phase).

The invention includes, in one embodiment, pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes, in one embodiment, derivatives of the SARM compounds (Compounds of formula I-V, 1-8). The term "derivatives" includes but is not limited to ether derivatives, acid derivatives, amide derivatives, ester derivatives and the like. In addition, this invention further includes hydrates of the SARM compounds (Compounds of formula I-V, 1-8). The term "hydrate" includes but is not limited to hemihydrate, monohydrate, dihydrate, trihydrate and the like.

This invention further includes, in one embodiment, metabolites of the SARM compounds (Compounds of formula I-V, 1-8). The term "metabolite" means any substance produced from another substance by metabolism or a metabolic process.

This invention further includes, in one embodiment, pharmaceutical products of the SARM compounds (Compounds of formula I-V, 1-8). The term "pharmaceutical product" means a composition suitable for pharmaceutical use (pharmaceutical composition), as defined herein.

This invention further includes, in one embodiment, prodrugs of the SARM compounds (Compounds of formula I-V, 1-8). The term "pro-drug" means a substance which can be converted in-vivo into a biologically active agent by such reactions as hydrolysis, esterification, desterification, activation, salt formation and the like.

This invention further includes, in one embodiment, crystals of the SARM compounds(Compounds of formula I-V, 1-8). Furthermore, this invention provides polymorphs of the SARM compounds. The term "crystal" means a substance in a crystalline state. The term "polymorph" refers, in one embodiment, to a particular crystalline state of a substance, having particular physical properties such as X-ray diffraction, IR spectra, melting point, and the like.

The AR is a ligand-activated transcriptional regulatory protein that mediates induction of male sexual development and function through its activity with endogenous androgens (male sex hormones). The androgenic hormones are steroids that are produced in the body by the testis and the cortex of the adrenal gland. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199-205 (1993) ("Sundaram")).

A receptor agonist is, in one embodiment, a substance that binds a receptor and activates it. A receptor partial agonist is, in one embodiment, a substance that binds a receptor and partially activates it. A receptor antagonist is, in one embodiment, a substance that binds a receptor and inactivates it. As demonstrated herein, the SARM compounds of the present invention have a tissue-selective effect, wherein one agent may be an agonist, partial agonist and/or antagonist, depending on the tissue. For example, the SARM compound may stimulate muscle tissue and at the same time inhibit prostate tissue. In one embodiment, the SARM compound is an AR agonist, and is, therefore, useful in binding to and activating the AR. In another embodiment, the SARM compound is an AR antagonist, and is, therefore, useful in binding to and inactivating the AR. Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds inhibit the growth of AR containing tissue.

In another embodiment, a SARM compound of the present invention (Compounds of formula I-V, 1-8) can be classified as a partial AR agonist/antagonist. In this embodiment, a SARM compound is an AR agonist in some tissues, causing increased transcription of AR-responsive genes (e.g. muscle anabolic effect). In other tissues, the compound serves as a competitive inhibitor of testosterone/DHT on the AR, preventing agonistic effects of native androgens.

In one embodiment, the SARM compound (Compounds of formula I-V, 1-8) of the present invention binds reversibly to the AR. In another embodiment, the SARM compound binds irreversibly to the AR. The compounds of the present invention may contain a functional group (affinity label) that allows alkylation of the AR (i.e. covalent bond formation). Thus, in this case, the compound binds irreversibly to the receptor and, accordingly, cannot be displaced by a steroid, such as the endogenous ligands DHT and testosterone.

"Anabolic activity" refers, in one embodiment, to increasing the mass of a connective tissue. In another embodiment, "anabolic activity" refers to increasing the strength of a connective tissue. In one embodiment, the connective tissue is cortical bone. In another embodiment, the connective tissue is trabecular bone. In another embodiment, the connective tissue is cancellous bone. In another embodiment, the connective tissue is muscle. In another embodiment, the connective tissue is cartilage. In another embodiment, the connective tissue is any other type of connective tissue known in the art. Increases in the weight of the levator ani muscle were used in the present invention to demonstrate anabolic activity, and are accepted in the art as a reliable index of anabolic activity (Antonio J et al, "Effects of castration and androgen treatment on androgen-receptor levels in rat skeletal muscles," J Appl Physiol 87: 2016-2019, 1999). Anabolic activity in bone and muscle synergize, in one embodiment, to decrease fracture rates in a subject.

In another embodiment, anabolic activity is a manifestation of AR agonistic activity in a connective tissue. Each type of anabolic activity represents a separate embodiment of the present invention.

For example, the findings described in Example 1 show that SARM compounds 1 and 2 are useful in treating ADAM-associated conditions, as evidenced by their androgenic and/or anabolic activity. "Androgenic activity" refers, in one embodiment, to androgen receptor (AR) agonist activity in androgenic target tissues, such as prostate and seminal vesicles. Androgenic effects were shown by increases in weights of the prostate and seminal vesicles, which are accepted in the art as indicators of androgenic activity (Almeida S A et al, Braz J Med Biol Res 31(11): 1443-8, November 1998; Lemus A E et al, J Steroid Biochem Mol Biol 60(1-2): 121-9, January 1997).

In another embodiment, the present invention provides a method of treating a male subject having an ADAM-associated condition, the method comprising administering to the subject a SARM compound of formula I-V, 1-8 or its analog, derivative, isomer, metabolite, pharmaceutically acceptable salt, pharmaceutical product, hydrate or N-oxide, pro-drug, polymorph or crystal thereof. In another embodiment, the method comprises administering a compound of formula I. In another embodiment, the method comprises administering a compound of formula II. In another embodiment, the method comprises administering a compound of formula III. In another embodiment, the method comprises administering a compound of formula IV. In another embodiment, the method comprises administering a compound of formula In another embodiment, the method comprises administering a compound of formula V. In another embodiment, the method comprises administering a compound of formula 1. In another embodiment, the method comprises administering a compound of formula 2. In another embodiment, the method comprises administering a compound of formula 3. In another embodiment, the method comprises administering a compound of formula 4. In another embodiment, the method comprises administering a compound of formula 5.

In one embodiment, the present invention provides a method of suppressing, inhibiting or reducing an incidence of an ADAM-associated condition in a male subject, the method comprising administering to the subject a SARM compound of formula I-V, 1-8 or its analog, derivative, isomer, metabolite, pharmaceutically acceptable salt, pharmaceutical product, hydrate or N-oxide, pro-drug, polymorph or crystal thereof. In another embodiment, the method comprises administering a compound of formula I. In another embodiment, the method comprises administering a compound of formula II. In another embodiment, the method comprises administering a compound of formula III. In another embodiment, the method comprises administering a compound of formula IV. In another embodiment, the method comprises administering a compound of formula In another embodiment, the method comprises administering a compound of formula V. In another embodiment, the method comprises administering a compound of formula 1. In another embodiment, the method comprises administering a compound of formula 2. In another embodiment, the method comprises administering a compound of formula 3. In another embodiment, the method comprises administering a compound of formula 4. In another embodiment, the method comprises administering a compound of formula 5.

In one embodiment, the present invention provides a method of treating a male subject having a sexual dysfunction, decreased sexual libido, erectile dysfunction, hypogonadism, sarcopenia, osteopenia, osteoporosis, an alteration in cognition and mood, depression, anemia, hair loss, obesity, muscle loss, BPH, dry eye, memory loss, or prostate cancer due ADAM, the method comprising administering to the subject a SARM compound of formula I-V, 1-8 or its analog, derivative, isomer, metabolite, pharmaceutically acceptable salt, pharmaceutical product, hydrate or N-oxide, pro-drug, polymorph or crystal thereof. In another embodiment, the method comprises administering a compound of formula I. In another embodiment, the method comprises administering a compound of formula II. In another embodiment, the method comprises administering a compound of formula III. In another embodiment, the method comprises administering a compound of formula IV. In another embodiment, the method comprises administering a compound of formula In another embodiment, the method comprises administering a compound of formula V. In another embodiment, the method comprises administering a compound of formula 1. In another embodiment, the method comprises administering a compound of formula 2. In another embodiment, the method comprises administering a compound of formula 3. In another embodiment, the method comprises administering a compound of formula 4. In another embodiment, the method comprises administering a compound of formula 5.

For example, the findings described in Example 1 show that SARM compounds 1 and 2 exhibit full agonist or mixed-agonist AR activity, depending on the target tissue, and that the degree of activity and tissue-specificity varies between different SARM compounds. Thus, particular SARM compounds can be chosen to treat particular ADAM-associated conditions, depending on the degree and type (agonist, mixed agonist, or antagonist) of AR activity required and the target tissues of importance.

In one embodiment, an anabolic activity of SARM compound is used in treating an ADAM-associated condition that is remediated by anabolic activity. In one embodiment, the condition is osteopenia. In another embodiment, the condition is osteoporosis. In another embodiment, the condition is obesity. In another embodiment, the condition is sarcopenia. The present invention (Examples 2 and 3) shows that SARM compounds are anabolic in both cortical and trabecular bone and muscle in testosterone-depleted subjects, and subjects with slight androgen depletion. In addition, SARM compounds were demonstrated to prevent bone resorption in response to androgen deprivation. Thus, SARM compounds have utility in (a) treating ADAM-associated conditions that are remediated by anabolic activity (e.g. reversing connective tissue loss); and (b) inhibiting or reducing the incidence of such ADAM-associated conditions (e.g. preventing connective tissue loss due to anticipated androgen deprivation.

Thus, in one embodiment, the subject of the present invention is androgen-depleted. In another embodiment, the subject is androgen deficient. In another embodiment, the subject has normal levels of androgen. In another embodiment, the subject will soon undergo a treatment that will deplete his androgen levels. In another embodiment, the subject is an aging male subject. Each possibility represents a separate embodiment of the present invention.

In the present invention, SARM compounds (Compounds of formula I-V, 1-8) were shown to have no effect on levels of testosterone, FSH, and LH. Thus, in one embodiment, the subject of the present invention is a subject in which therapy that affects testosterone, FSH, or LH levels is contra-indicated. In one embodiment, the subject for whom such therapy is contra-indicated is a subject at risk for anosmia, visual abnormalities, or headaches. In another embodiment, the subject or his/her physician wishes to avoid affecting levels of testosterone, FSH, and LH to avoid aggravating an ADAM-associated condition.

In another embodiment, the male subject of the present invention is an aging male subject. In one embodiment, the term "aging" means a process of becoming older. In one embodiment, the aging male is a male over 40 years old. In another embodiment, the aging male is a male over 45 years old. In another embodiment, the aging male is a male over 45 years old. In another embodiment, the aging male is a male over 50 years old. In another embodiment, the aging male is a male over 55 years old. In another embodiment, the aging male is a male over 60 years old. In another embodiment, the aging male is a male over 65 years old. In another embodiment, the aging male is a male over 70 years old. In another embodiment, the aging male is a male over 75 years old.

In another embodiment, an androgenic activity of a SARM compound (Compounds of formula I-V, 1-8) is used to treat an ADAM-related condition. In one embodiment, the condition is sexual dysfunction. In another embodiment, the condition is osteoporosis. In another embodiment, the condition is obesity. In another embodiment, the condition is sarcopenia. In another embodiment, the condition is decreased sexual libido. In another embodiment, the condition is erectile dysfunction. In another embodiment, the condition is hypogonadism. In another embodiment, the condition is an alteration in cognition and mood. In another embodiment, the condition is depression. In another embodiment, the condition is BPH. In another embodiment, the condition is anemia. In another embodiment the condition is muscle loss. In another embodiment the condition is dry eye. In another embodiment the condition is memory loss.

The present invention shows that SARM compounds (Compounds of formula I-V, 1-8) exhibit AR mixed agonist activity in androgenic target tissues such as prostate and seminal vesicles. Since the level and type of AR activity and the affected tissues vary between different SARM compounds, it is possible to choose the appropriate SARM compound based on the type of AR activity and the target tissue desired.

Thus, in another embodiment, an antagonistic AR activity of a SARM compound (Compounds of formula I-V, 1-8) in an androgenic target tissue is used to treat an ADAM-related condition. In one embodiment, the condition is BPH. In another embodiment, the condition is hair loss. In another embodiment, the condition is prostate cancer.

In one embodiment, the ADAM-associated condition is sexual dysfunction. In one embodiment, the sexual dysfunction is a desire disorders. In another embodiment, the sexual dysfunction is an arousal disorders. In another embodiment, the sexual dysfunction is an orgasm disorder. In another embodiment, the sexual dysfunction is a pain disorder. Each type of sexual dysfunction represents a separate embodiment of the present invention.

In another embodiment, the ADAM-associated condition is decreased sexual libido. The term "libido, in one embodiment, means sexual desire.

In another embodiment, the ADAM-associated condition is erectile dysfunction. The term "erectile," in one embodiment, means capable of being erected. An erectile tissue is a tissue which is capable of being greatly dilated and made rigid by the distension of the numerous blood vessels which it contains.

In another embodiment, the ADAM-associated condition is hypogonadism. "Hypogonadism," in one embodiment, is a condition resulting from or characterised by abnormally decreased functional activity of the gonads, with retardation of growth and sexual development.

In another embodiment, the ADAM-associated condition is sarcopenia. In one embodiment, the sarcopenia comprises muscle loss. In another embodiment, the sarcopenia comprising weight loss. In another embodiment, the sarcopenia is any other definition of sarcopenia known in the art. Each definition of sarcopenia represents a separate embodiment of the present invention.

In another embodiment, the ADAM-associated condition is osteopenia. "Osteopenia" refers, in one embodiment, to decreased calcification or density of bone. This is a term which encompasses, in one embodiment, all skeletal systems in which such a condition is noted.

In another embodiment, the ADAM-associated condition is osteoporosis. "Osteoporosis" refers, in one embodiment, to a thinning of the bones with reduction in bone mass due to depletion of calcium and bone protein. Osteoporosis predisposes a person to fractures, which are often slow to heal and heal poorly. Unchecked osteoporosis can lead to changes in posture, physical abnormality, and decreased mobility.

"Osteoporosis" refers, in another embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

Osteoporosis and osteopenia are, in another embodiment, systemic skeletal diseases characterized by low bone mass and microarchitectural deterioration of bone tissue. "Microarchitectural deterioration" refers, in one embodiment, to thinning of the trabeculae (defined below) and the loss of inter-trabecular connections in bone. In another embodiment, "osteoporosis" is defined as having a BMD 2.5 standard deviations (SD) or more below the young adult mean. In another embodiment, "osteoporosis" is defined as having a BMC 2.5 SD or more below the young adult mean. In another embodiment, "osteoporosis" is defined as having a BMD 2.0 SD or more below the young adult mean. In another embodiment, "osteoporosis" is defined as having a BMC 2.0 SD or more below the young adult mean. In another embodiment, "osteoporosis" is defined as having a BMD 3.0 SD or more below the young adult mean. In another embodiment, "osteoporosis" is defined as having a BMC 3.0 SD or more below the young adult mean. Each definition of osteoporosis or osteopenia represents a separate embodiment of the present invention.

In another embodiment, the ADAM-associated condition is BPH. BPH is, in one embodiment, a nonmalignant enlargement of the prostate gland, and is the most common nonmalignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra that traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

In another embodiment, the ADAM-associated condition is associated with an alternation in cognition and mood. The term "cognition" refers, in one embodiment, to the process of knowing, specifically the process of being aware, knowing, thinking, learning and judging. Cognition is related to the fields of psychology, linguistics, computer science, neuroscience, mathematics, ethology and philosophy. The term "mood" refers, in one embodiment, to a state of the mind. In another embodiment, "mood" refers to a tendency to anger. In another embodiment, "mood" refers to a tendency to sadness. As contemplated herein, "alterations" means, in one embodiment, any change for the positive or negative, in cognition and/or mood.

In another embodiment, the ADAM-associated condition is depression. The term "depression" refers, in one embodiment, to an illness that involves the body, mood and thoughts, that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In another embodiment, the ADAM-associated condition is hair loss. The term "hair loss", medically known as alopecia, refers, in one embodiment, to baldness. In one embodiment, the baldness is male-pattern baldness. Baldness typically begins with patch hair loss on the scalp and sometimes progresses to complete baldness and even loss of body hair. Hair loss affects both males and females.

In another embodiment, the ADAM-associated condition is anemia. "Anemia" refers, in one embodiment, to the condition of having less than the normal number of red blood cells or less than the normal quantity of hemoglobin in the blood. The oxygen-carrying capacity of the blood is, therefore, decreased. Persons with anemia may feel tired and fatigue easily, appear pale, develop palpitations and become usually short of breath. Anemia is caused by four basic factors: a) hemorrhage (bleeding); b) hemolysis (excessive destruction of red blood cells); c) underproduction of red blood cells; and d) not enough normal hemoglobin. There are many forms of anemia, including aplastic anemia, benzene poisoning, Fanconi anemia, hemolytic disease of the newborn, hereditary spherocytosis, iron deficiency anemia, osteopetrosis, pernicious anemia, sickle cell disease, thalassemia, myelodysplastic syndrome, and a variety of bone marrow diseases. As contemplated herein, the SARM compounds of the present invention are useful in preventing and/or treating any one or more of the above-listed forms of anemia.

In another embodiment, the ADAM-associated condition is obesity. "Obesity" refers, in one embodiment, to the state of being well above one's normal weight. Traditionally, a person is considered to be obese if they are more than 20 percent over their ideal weight. Obesity has been more precisely defined by the National Institute of Health (NIH) as a Body to Mass Index (BMI) of 30 or above. Obesity is often multifactorial, based on both genetic and behavioral factors. Overweight due to obesity is a significant contributor to health problems. It increases the risk of developing a number of diseases including: Type 2 (adult-onset) diabetes; high blood pressure (hypertension); stroke (cerebrovascular accident or CVA); heart attack (myocardial infarction or MI); heart failure (congestive heart failure); cancer (certain forms such as cancer of the prostate and cancer of the colon and rectum); gallstones and gallbladder disease (cholecystitis); Gout and gouty arthritis; osteoarthritis (degenerative arthritis) of the knees, hips, and the lower back; sleep apnea (failure to breath normally during sleep, lowering blood oxygen); and Pickwickian syndrome (obesity, red face, underventilation and drowsiness). As contemplated herein, the term "obesity" includes any one of the above-listed obesity-related conditions and diseases. Thus the SARM compounds of the present invention are useful in preventing and/or treating obesity and any one or more of the above-listed obesity-related conditions and diseases.

In another embodiment, the ADAM-associated condition is prostate cancer. Prostate cancer is one of the most frequently occurring cancers among men in the United States, with hundreds of thousands of new cases diagnosed each year. Over sixty percent of newly diagnosed cases of prostate cancer are found to be pathologically advanced, with no cure and a dismal prognosis. One third of all men over 50 years of age have a latent form of prostate cancer that may be activated into the life-threatening clinical prostate cancer form. The frequency of latent prostatic tumors has been shown to increase substantially with each decade of life from the 50s (5.3-14%) to the 90s (40-80%). The number of people with latent prostate cancer is the same across all cultures, ethnic groups, and races, yet the frequency of clinically aggressive cancer is markedly different. This suggests that environmental factors may play a role in activating latent prostate cancer. Methods of diagnosing prostate cancer are well known in the art, and include measurement of free- and bound prostate-specific antigen (PSA) prostate exam, and prostate biopsy.

Each ADAM-related condition treated by a SARM compound (Compounds of formula I-V, 1-8) represents a separate embodiment of the present invention. Each type of AR activity (agonistic, partial agonistic, and antagonistic represents a separate embodiment of the present invention. Each target tissue represents a separate embodiment of the present invention.

The present invention further provides a class of compounds referred to as SARM compounds. Each of these compounds (Compounds of formula I-V, 1-8) acts, in one embodiment, as either an androgen receptor (AR) agonist, partial agonist and/or antagonist, depending on the tissue.

In another embodiment, the SARM compounds of the present invention (Compounds of formula I-V, 1-8) may be categorized into subgroups depending on their biological activity. For example, several SARM compounds have an agonistic effect on muscle or bone. Other SARM compounds have no effect on muscle or bone. Other SARM compounds have no effect or an antagonistic effect on prostate. Other SARM compounds are able to penetrate the central nervous system (CNS). Other SARM compounds do not penetrate the CNS. Each subgroup of SARM compounds represents a separate embodiment of the present invention.

For example, one subgroup of SARM compounds has no effect on muscle and bone, and have neutral or antagonistic effect on prostate. Within this subgroup, those SARM compounds that do not penetrate the CNS are effective, in one embodiment, in treating or preventing BPH (BPH). Those SARM compounds that are able to penetrate the CNS are effective, in one embodiment, at treating or preventing sexual dysfunction.

Furthermore, another subgroup of SARM compounds has an agonistic activity on muscle and bone, and has a neutral or antagonistic effect on prostate. Within this subgroup, those SARM compounds that do not penetrate the CNS are effective, in one embodiment, at treating or preventing sarcopenia and osteopenia. Those SARM compounds that are able to penetrate the CNS are effective, in one embodiment, at treating or preventing hypogonadism, sexual dysfunction, sarcopenia and osteopenia.

Pharmaceutical Compositions

The treatment methods of the present invention comprise, in one embodiment, administering a pharmaceutical preparation comprising the SARM compound of formula I-V, 1-8 and/or its analog, derivative, isomer, metabolite, pharmaceutically acceptable salt, pharmaceutical product, hydrate, N-oxide, pro-drug, polymorph, crystal or any combination thereof; and a pharmaceutically acceptable carrier.

As used herein, "pharmaceutical composition" means a composition comprising an "effective amount" of the active ingredient, i.e. the SARM compound, together with a pharmaceutically acceptable carrier or diluent.

An "effective amount" refers, in one embodiment, to that amount which provides a therapeutic effect for a given condition and administration regimen. An "effective amount" of the SARM compounds as used herein can be in the range of 1-500 mg/day. In one embodiment the dosage is in the range of 1-100 mg/day. In another embodiment the dosage is in the range of 100-500 mg/day. In another embodiment the dosage is in a range of 45-60 mg/day. In another embodiment the dosage is in the range of 15-25 mg/day. In another embodiment the dosage is in the range of 55-65 mg/day. In another embodiment the dosage is in the range of 45-60 mg/day. The SARM compounds can be administered daily, in single dosage forms containing the entire amount of daily dose, or can be administered daily in multiple doses such as twice daily or three times daily. The SARM compounds can also be administered intermittently, for example every other day, 3 days a week, four days a week, five days a week and the like.

The terms "treating" and "treatment" refer, in one embodiment, curative treatment. In another embodiment, the terms refer to lessening the severity of a disorder. In another embodiment, the terms refer to lessening the frequency of outbreaks of a disorder. In another embodiment, the terms refer to remitative treatment of a disorder (i.e. treatment that causes the disorder to enter remission). The terms "reducing", "suppressing" and "inhibiting" refer, in one embodiment, to lessening or decreasing.

The term "administering" refers, in one embodiment, to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject. In one embodiment, the subject is a mammalian subject. In another embodiment, the subject is a human.

The pharmaceutical compositions containing the SARM agent can be administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulstions, oils and the like. In one embodiment of the present invention, the SARM compounds are formulated in a capsule. In accordance with this embodiment, the compositions of the present invention comprise in addition to the SARM active compound and the inert carrier or diluent, a hard gelating capsule.

Further, in another embodiment, the pharmaceutical compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intra-muscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which the entire SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions that contain an active component is well understood in the art, for example by mixing, granulating, or tablet-forming processes. The active therapeutic ingredient is often mixed with excipients that are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM of formula I-V, 1-8 will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, the methods of the present invention comprise administering a SARM compound of formula I-V or 1-8 as the sole active ingredient. However, also encompassed within the scope of the present invention are methods for treating and/or preventing ADAM-associated conditions as described herein, which comprise administering the SARM compounds in combination with one or more therapeutic agents. These agents include, but are not limited to: LHRH analogs, reversible anti-androgens, antiestrogens, anticancer drugs, 5-alpha reductase inhibitors, aromatase inhibitors, progestins, or agents acting through other nuclear hormone receptors.

Thus, in one embodiment, the present invention provides compositions and pharmaceutical compositions comprising a selective AR modulator compound of formula I-V or 1-8, in combination with an LHRH analog. In another embodiment, the present invention provides compositions and pharmaceutical compositions comprising a selective AR modulator compound of formula I-V or 1-8, in combination with a reversible anti-androgen. In another embodiment, the present invention provides compositions and pharmaceutical compositions comprising a selective AR modulator compound of formula I-V or 1-8, in combination with an antiestrogen. In another embodiment, the present invention provides compositions and pharmaceutical compositions comprising a selective AR modulator compound of formula I-V or 1-8, in combination with an anticancer drug. In another embodiment, the present invention provides compositions and pharmaceutical compositions comprising a selective AR modulator compound of formula I-V or 1-8, in combination with a 5-alpha reductase inhibitor. In another embodiment, the present invention provides compositions and pharmaceutical compositions comprising a selective AR modulator compound of formula I-V or 1-8, in combination with an aromatase inhibitor. In another embodiment, the present invention provides compositions and pharmaceutical compositions comprising a selective AR modulator compound of formula I-V or 1-8, in combination with a progestin. In another embodiment, the present invention provides compositions and pharmaceutical compositions comprising a selective AR modulator compound of formula I-V or 1-8, in combination with an agent acting through other nuclear hormone receptors.

The following examples are presented in order to more fully illustrate the preferred embodiments of the invention. They should in no way, however, be construed as limiting the broad scope of the invention.

EXPERIMENTAL SECTION

Example 1

Compound 1 and Compound 2 Exhibit Tissue-Specific Anabolic and Androgenic Activity in Rats of Varying Hormonal Status A study was performed to compare the pharmacologic effects and tissue-selectivity of 2 SARM compounds—Compound 1 and Compound 2—with testosterone propionate (TP) in male rats of varying hormonal status. Male rats with normal testicular function (i.e., intact with no surgical manipulation) were included to examine the effects of these compounds on subjects with normal blood levels of testosterone. Male rats that received unilateral orchidectomy (i.e., surgical removal of one testis) were included to examine the effects of these compounds on subjects with slight androgen depletion. Male rats that received bilateral orchidectomy (i.e., surgical removal of both testes) were included to examine the effects of these compounds on androgen-deficient subjects.

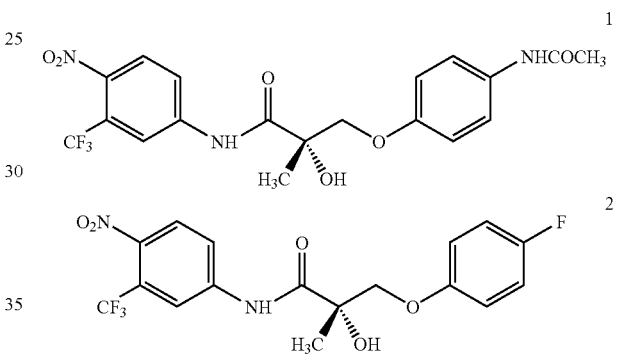

Methods

Compound 1 and Compound 2 were synthesized according to the procedures disclosed in U.S. Pat. No. 6,995,284. Male Sprague-Dawley rats were purchased from Harlan Biosciences (Indianapolis, Ind.). The animals were maintained on a 12-h cycle of light and dark with food and water available ad libitum. All animal studies were reviewed and approved by the Animal Care and Use Committee of The Ohio State University, and conformed to the Principles of Laboratory Animal Care (NIH publication #85-23, revised 1985). Immature male Sprague-Dawley rats weighing 187 to 214 g were randomly distributed into 9 groups of 5 animals. One day before the initiation of drug treatment, groups 4 through 6 and groups 7 through 9 received unilateral or bilateral orchidectomy, respectively, via a midline scrotal incision. Groups 1 through 3 did not undergo surgery. All drugs given to animals were freshly prepared as solutions in polyethylene glycol 300 (PEG 300). Groups 4 and 7 received treatment with vehicle alone (i.e., PEG 300). Animals in groups 3, 6, and 9 received testosterone propionate (TP, 0.5 mg/day) via implantation of subdermal osmotic pumps (Model 2002, Durect Corporation, Palo Alto, Calif.). Animals in groups 2, 5, and 8 received Compound 1 or Compound 2 (0.5 mg/day) via implantation of subdermal osmotic pumps. After 14 days of drug treatment, rats were weighed, anesthetized, and sacrificed. No adverse pharmacologic effects were observed upon administration of Compounds 1 and 2. Blood samples were collected by venipuncture of the abdominal aorta. Plasma samples were analyzed for testosterone, Follicle Stimulating Hormone (FSH), Luteinizing Hormone (LH) and osteocalcin. Testosterone concentrations were measured by AniLytics Inc. (Gaithersburg, Md.). FSH and LH levels were measured by the National Hormone and Peptide Program (Dr. A F Parlow, UCLA, CA). Plasma osteocalcin levels were determined using a commercially available rat osteocalcin EIA kit from Biomedical Technologies Inc. (Stoughton, Mass.). The ventral prostates, seminal vesicles, and levator ani muscle were removed and weighed. Osmotic pumps were also removed from animals to check for correct pump operation. The weights of all organs were normalized to body weight, and analyzed for any statistically significant differences between groups using single-factor ANOVA with the alpha value set a priori at $p<0.05$. The weights of prostates and seminal vesicles were used as indices for evaluation of androgenic activity, and the levator ani muscle weight was used to evaluate the anabolic activity. Statistical analyses of parameters from complete blood count or serum chemical profiling, wherever applicable, were performed by single-factor ANOVA with the alpha value set a priori at $p<0.05$.

Measurement of Anabolic and Androgenic Activity.

In vivo pharmacologic activities were determined by weight (% of intact control) of levator ani muscle, an indicator of anabolic activity. Bone formation rate, another indication of anabolic activity, was assessed by osteocalcin level measurement, as described above. Prostate and seminal vesicle were used as target tissues to indicate androgenic effects.

Results

Plasma testosterone levels were significantly lower in castrated rats, regardless of the treatment group (Table 1), while unilateral orchidectomy led to a decrease relative to intact controls that was not statistically significant. Administration of exogenous TP raised testosterone levels relative to vehicle-treated and Compound 1 treated controls in castrated rats, but not in hemi-orchidectomized animals. Compound 1 treatment did not affect testosterone levels in intact, hemi-orchidectomized or castrated male rats, demonstrating that Compound 1 has no significant effect on endogenous androgen production at pharmacologically relevant doses.

TABLE 1

Plasma testosterone levels (ng/ml) in different treatment groups (n = 5).

|  | Control | Compound 1 (0.5 mg/day) | TP (0.5 mg/day) |
|---|---|---|---|
| Intact | 2.674 ± 1.476 | 1.830 ± 0.510 | 1.482 ± 0.416 |
| Hemi-orchidec-tomized | 1.740 ± 1.049 | 1.404 ± 0.810 | 2.366 ± 1.232 |
| Castrated | 0.036 ± 0.075†‡ | 0.066 ± 0.148†‡ | 0.258 ± 0.103*†‡ |

*$p < 0.05$ compared to control group.
†$p < 0.05$ compared to intact group.
‡$p < 0.05$ compared to hemi-orchidectomized group.

Plasma FSH and LH levels significantly increased in castrated animals, but not in hemi-orchidectomized animals (Tables 2 and 3), corroborating the observation that unilateral orchidectomy had no large effect on plasma testosterone levels or the pituitary hormones that regulate it. Treatment with Compound 1 did not significantly affect FSH and LH levels in castrated male rats, while treatment with TP significantly decreased these levels compared to the untreated castrated animals, indicating that TP, but not Compound 1, suppresses pituitary hormone production. No treatments significantly affected FSH or LH levels in intact or hemi-orchidectomized animals.

These findings indicate that Compound 1 has no effect on pituitary hormone production. Thus, SARMs have a therapeutic advantage over testosterone in patients in which suppression of FSH or LH levels is contra-indicated.

TABLE 2

Plasma FSH levels (ng/ml) in different treatment groups (n = 5).

|  | Control | Compound 1 (0.5 mg/day) | TP (0.5 mg/day) |
|---|---|---|---|
| Intact | 13.0 ± 1.3 | 14.4 ± 1.7 | 11.4 ± 1.7 |
| Hemi-orchidectomized | 18.0 ± 1.9† | 15.2 ± 2.2 | 17.2 ± 3.3† |
| Castrated | 68.6 ± 6.3†‡ | 69.6 ± 11.7†‡ | 58.0 ± 6.9*†‡ |

*$p < 0.05$ compared to control group.
†$p < 0.05$ compared to intact group.
‡$p < 0.05$ compared to hemi-orchidectomized group.

TABLE 3

Plasma LH levels (ng/ml) in different treatment groups (n = 5).

|  | Control | Compound 1 (0.5 mg/day) | TP (0.5 mg/day) |
|---|---|---|---|
| Intact | 0.160 ± 0.187 | 0.026 ± 0.037 | 0.168 ± 0.173 |
| Hemi-orchi-dec-tomized | 0.240 ± 0.268 | 0.124 ± 0.115 | 0.124 ± 0.092 |
| Castrated | 8.704 ± 1.709†‡ | 8.644 ± 2.799†‡ | 6.702 ± 1.513†‡ |

*$p < 0.05$ compared to control group.
†$p < 0.05$ compared to intact group.
‡$p < 0.05$ compared to hemi-orchidectomized group.

In order to assess the effects of these treatments on osteoporosis, plasma osteocalcin levels were measured. Osteocalcin is a specific osteoblastic marker that can be used to evaluate the endogenous bone formation rate. Treatment with Compound 1 significantly increased plasma osteocalcin levels in hemi-orchidectomized and castrated animals, while TP had no effect on osteocalcin levels, as shown in Table 4. There were no significant differences in osteocalcin levels between intact, hemi-orchidectomized and castrated animals in the vehicle-treated (i.e., control) animals.

These findings demonstrated that Compound 1 increases bone formation rate in male subjects with both slight and severe androgen depletion, while having no effects on testosterone, FSH, or LH levels.

TABLE 4

Plasma osteocalcin levels (ng/ml) in different treatment groups (n = 5).

|  | Control | Compound 1 (0.5 mg/day) | TP (0.5 mg/day) |
|---|---|---|---|
| Intact | 59.403 ± 13.933 | 55.584 ± 9.715 | 74.952 ± 15.399 |
| Hemi-orchidec-tomized | 62.110 ± 14.770 | 89.804 ± 15.517*† | 77.236 ± 24.418 |
| Castrated | 66.965 ± 11.305 | 94.215 ± 12.568*† | 65.976 ± 11.213 |

*$p < 0.05$ compared to control group.
†$p < 0.05$ compared to intact group.
‡$p < 0.05$ compared to hemi-orchidectomized group.

Figure 3A:
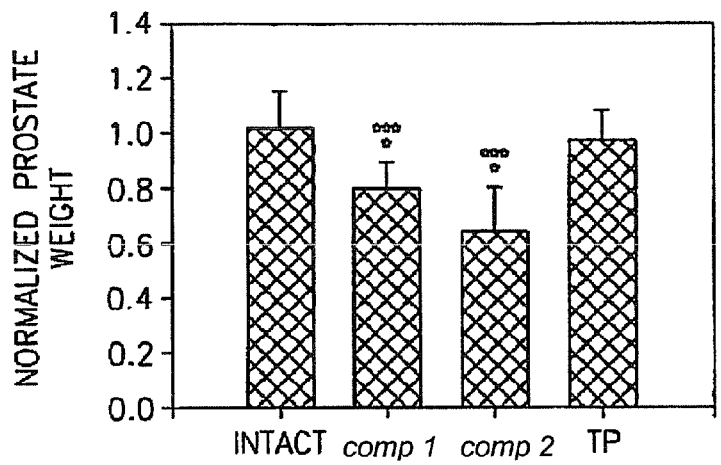
FIG. 3: Androgenic and anabolic activity of Compound 1 and Compound 2 in rats. Male rats with normal testicular function (no surgical manipulation) were left untreated (Intact), treated with compound 1 (0.5 mg/day), compound 2 (0.5 milligram (mg)/day) or testosterone proprionate (TP, 0.5 mg/day), and the weight of androgen-responsive tissues (prostate—FIG. 3A, seminal vesicles—FIG. 3B, and levator ani muscle—FIG. 3C) was determined.
Figure 3B:
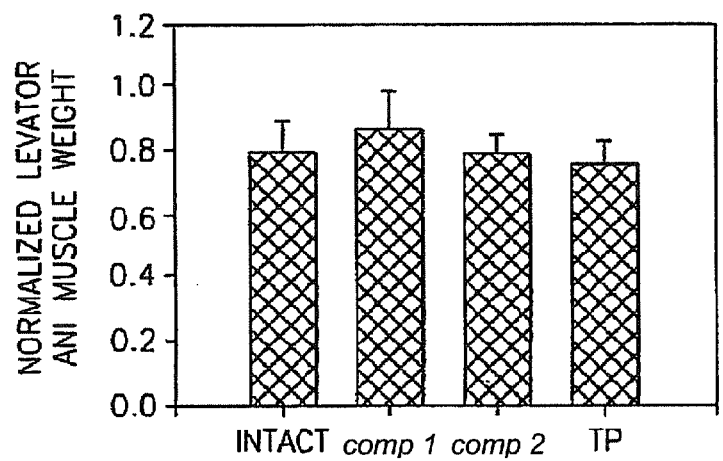
Figure 3C:
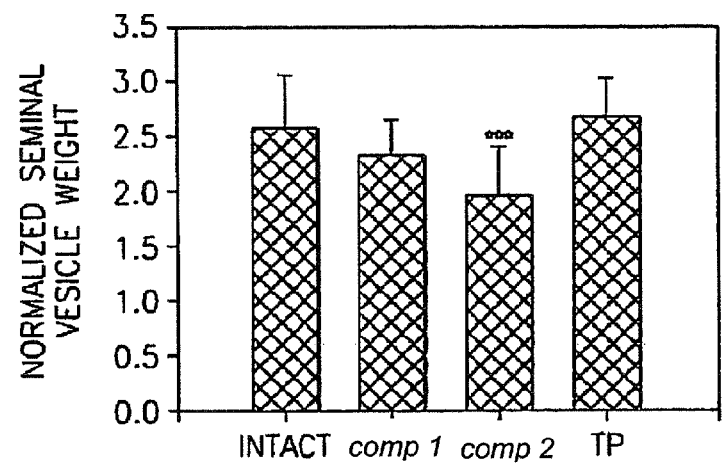

In intact animals, Compounds 1 and 2 decreased the size of the prostate to 79% and about 61% of control animals (Table 5; FIG. 3A). In addition, Compound 2, but not Compound 1, significantly decreased the size of the seminal vesicles (FIG. 3B). Neither Compound 1 nor Compound 2 significantly affected the size of the levator ani muscle (FIG. 3C).

Figure 4A:
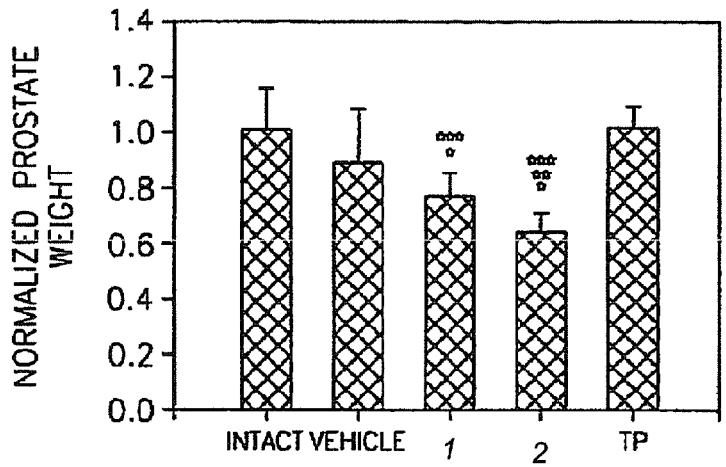
FIG. 4: Androgenic and anabolic activity of Compound 1 and Compound 2 in rats. Male rats received unilateral orchidectomy (Hemi-orchidectomized) and were left untreated (Intact), treated with vehicle alone (PEG 300), Compound 1 (0.5 mg/day), Compound 2 (0.5 mg/day), or testosterone proprionate (TP, 0.5 mg/day), and the weight of androgen-responsive tissues (prostate—FIG. 4A, seminal vesicles—FIG. 4B, and levator ani muscle—FIG. 4C) was determined.
Figure 4B:
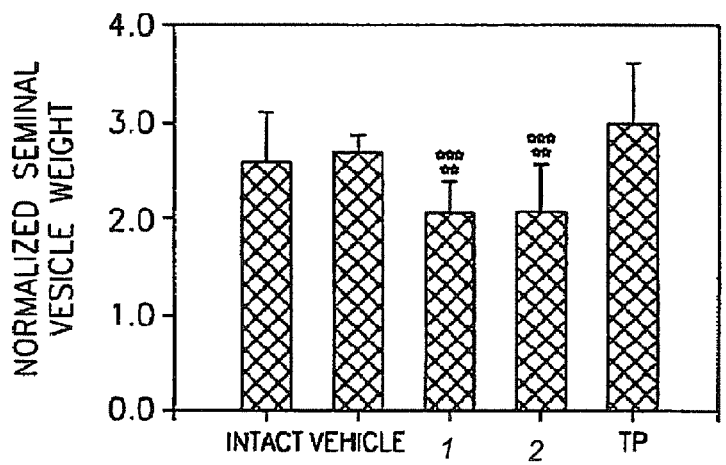
Figure 4C:
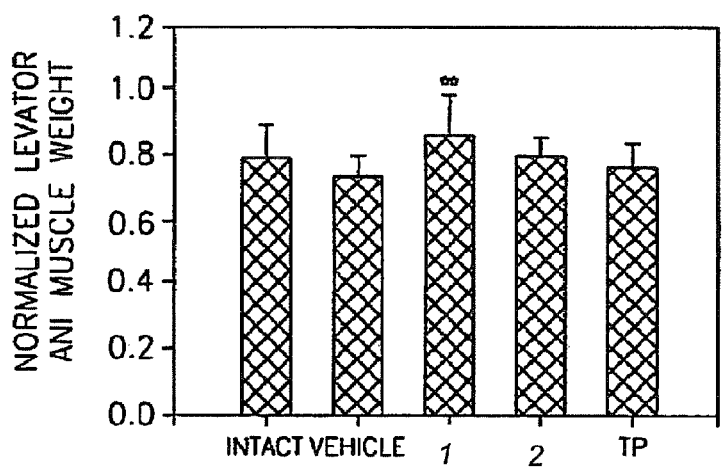

Compounds 1 and 2 also exhibited tissue selective pharmacologic effects in hemi-orchidectomized animals (Table 5 and FIG. 4). Compounds 1 and 2 decreased the size of the prostate to 75% and 60%, respectively (FIG. 4A), and each decreased the size of the seminal vesicles to 75% (FIG. 4B). Compound 1 increased the size of the levator ani muscle (FIG. 4C) to 108% of untreated hemi-orchidectomized animals.

Figure 5A:
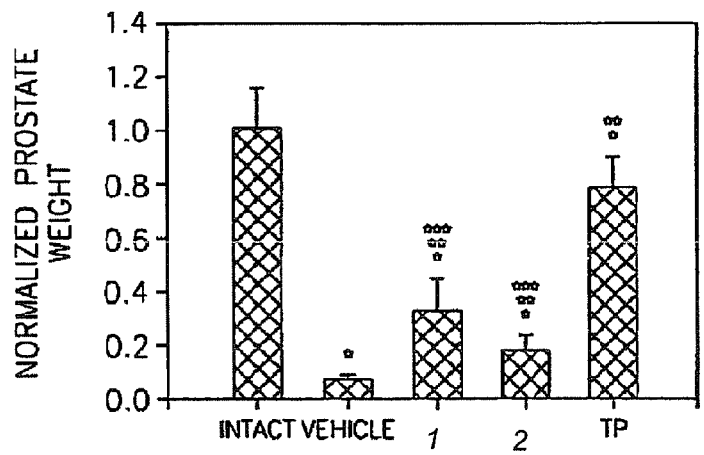
FIG. 5: Androgenic and anabolic activity of Compound 1 and Compound 2 in rats. Male rats received bilateral orchidectomy (Castrated) and were left untreated (Intact), treated with vehicle alone (PEG 300), Compound 1 (0.5 mg/day), Compound 2 (0.5 mg/day), or testosterone proprionate 0.5 mg/day), and the weight of androgen-responsive tissues (prostate—FIG. 5A, seminal vesicles—FIG. 5B, and levator ani muscle—FIG. 5C) was determined.
Figure 5B:
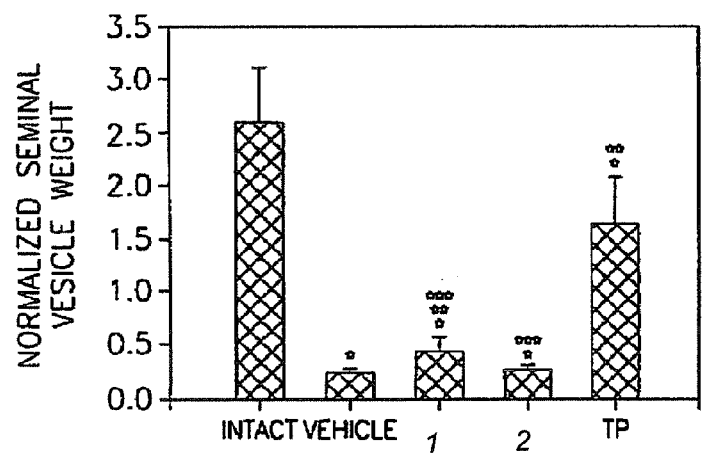
Figure 5C:
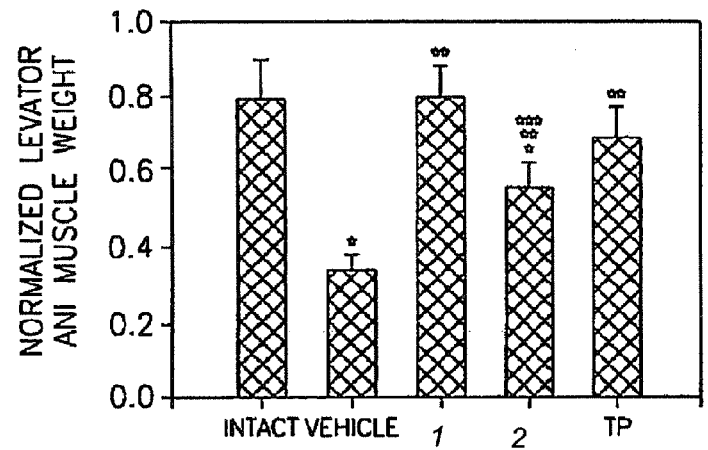
Figure 6A:
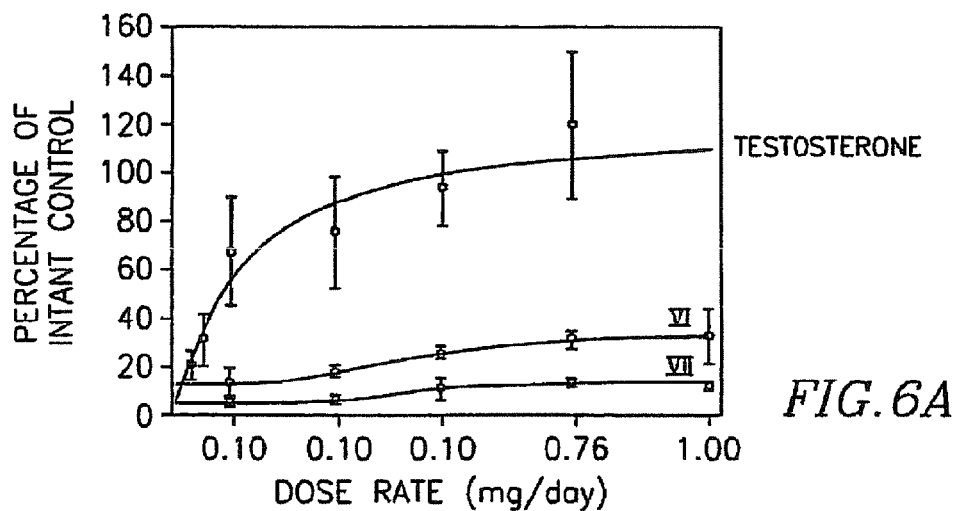
FIG. 6: Dose response Curves. Rats were left untreated, or treated with 0.1, 0.3, 0.5, 0.75 and 1.0 mg/day Compound 1 Compound 2 or testosterone propionate (TP), and the weight of androgen-responsive tissues (prostate—FIG. 6A, seminal vesicles—FIG. 6B and levator ani muscle—FIG. 6C) was determined. The results are plotted as percentage of the intact control.
Figure 6B:
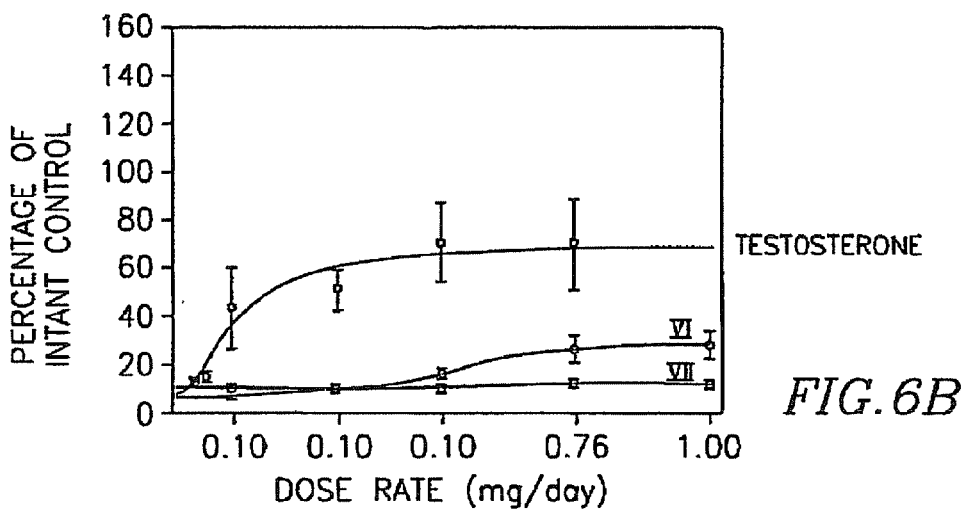
Figure 6C:
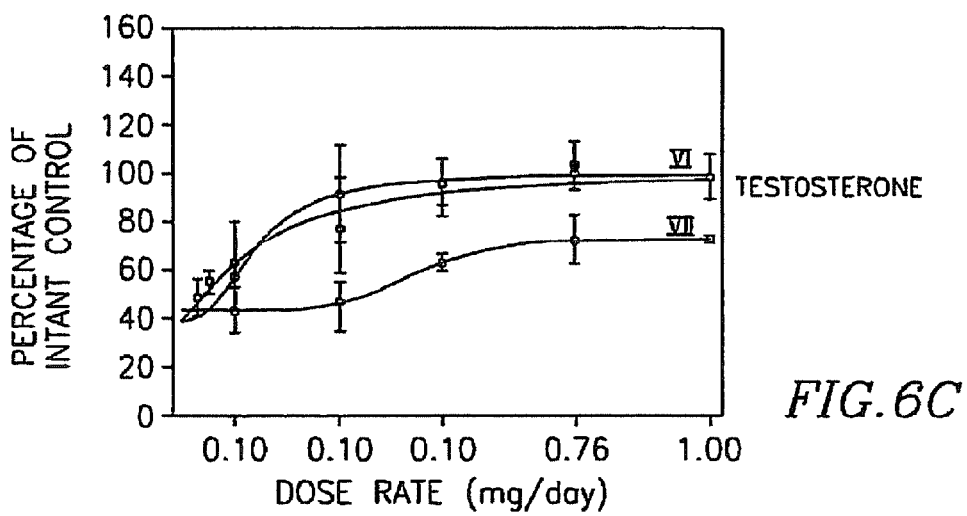

In castrated animals, as shown in Table 5 and in FIGS. 5 and 6, Compounds 1 and 2 increased the size of the prostate (FIG. 5A and FIG. 6A), seminal vesicles (FIG. 5B and FIG. 6B), and the levator ani muscle (FIG. 5C and FIG. 6C). In all cases of the castrated animals, differences between the SARM-treated animals and the untreated, castrated animals were statistically significant except for the seminal vesicle weight in the Compound 2-treated animals. Of note, the ratio of the anabolic activity to the androgenic activity was greater for the SARMS than for TP.

Thus, Compound 1 acts as a partial AR agonist in prostate and seminal vesicles and as a full AR agonist in levator ani muscle, while Compound 2 acts as a partial agonist in all tissues studied.

The findings of this Example demonstrate that (a) SARM compounds exhibit tissue selective pharmacologic effects on the AR; (b) SARM compounds exhibit anabolic activity in the absence of equally strong androgenic activity; (c) SARM compounds do not affect testosterone, FSH, or LH levels; and (d) tissue-specificity of the AR agonistic or antagonistic activity of SARM compounds is different from testosterone, and varies as well between different SARM compounds. Thus, SARM compounds are useful for a variety of ADAM-related disorders and diseases. Selection of the particular SARM will depend on the type of AR activity and target tissue of interest.

Example 2

Effect of Compound 1 on Myosin Heavy Chain (Mhc) Subtype IIb mRNA Expression

Methods

Expression of myosin heavy chain (MHC) subtypes was examined using RT-PCR of masseter muscle tissue of female rats by the method of Wright C et al, (Analysis of myosin heavy chain mRNA expression by RT-PCR, J Appl Physiol. 1997 October; 83(4): 1389-96). MHC is the predominant protein in skeletal muscle, is encoded by a multigene family, and is expressed in a tissue-specific and developmentally regulated manner (Adams G R et al, Time course of myosin heavy chain transitions in neonatal rats: importance of innervation and thyroid state, Am J Physiol. 1999 April; 276(4 Pt 2): R954-61). At steady state, mRNA expression parallels the pattern of MHC protein expression. Because transcription of MHC mRNA occurs in advance of MHC protein translation, and the increased sensitivity of RT-PCR compared to western blotting, rapid changes in mRNA expression can be detected and used to analyze the subtle dynamic effects on muscle metabolism.

Results

Figure 7A:
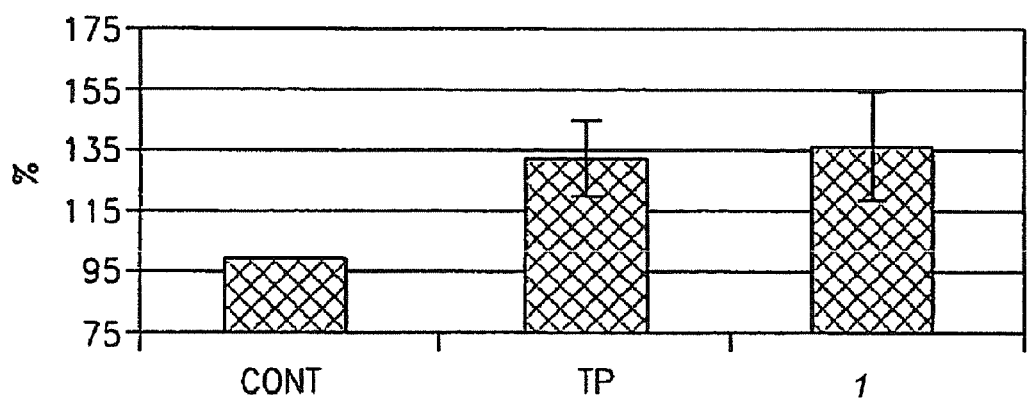
FIG. 7A: histogram showing effect of Compound 1 on MEIC IIb mRNA expression.
Figure 7B:
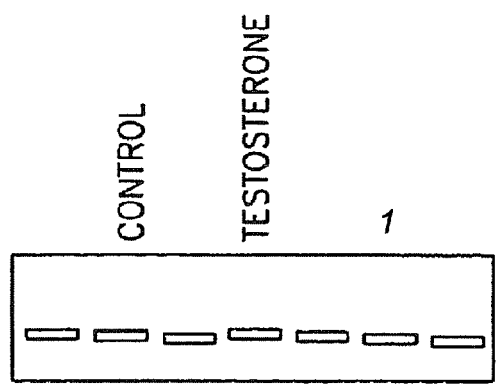
FIG. 7B: raw RT-PCR data, showing MHC IIb mRNA expression.

Anabolic activity of Compound 1 on muscle was tested by assessing expression of MHC subtypes in skeletal muscle. MHC IIb expression level in masseter muscle of intact rats was set as the standard (100%) (FIG. 7A). TP and Compound 1 both exhibited an anabolic effect on masseter muscle, increasing transcription of MHC type IIb to 133% and 137% of the untreated control (FIG. 7A). Actual untransformed PCR data is depicted in FIG. 7B.

The findings of this Example show that SARM compounds are anabolic in muscle tissue.

Example 3

Effect of SARM Compounds on Bone Resorption in Rats

This study assessed the affect of SARM compounds on bone resorption in osteoporotic subjects. One hundred ten female rats were assigned to one of eleven treatment groups. Groups 1-3 were intact animals, and groups 4-12 were ovariectomized on day one of the study. Groups 1 and 4 received on drug treatment, and groups 2 and 5 received dihydrotestosterone (DHT) at a dose of 1 mg/day. Groups 7-12 received Compound 1 via daily subcutaneous injection at doses of 0.1, 0.3, 0.5, 0.75, 1.0, and 3 mg/day, respectively. Groups 3 and 6 received Compound 1 at a dose of 1.0 mg/day together with the anti-androgen bicalutamide, to ascertain whether observed effects were mediated by the AR. All animals were treated for 120 days. Bone mineral content (BMC) was determined using dual energy x-ray absorptiometry (DEXA) on days 1, 30, 60, 90, and 120. Drug administration began immediately after oopherectomy (i.e., on the day that the operation was performed).

Figure 8:
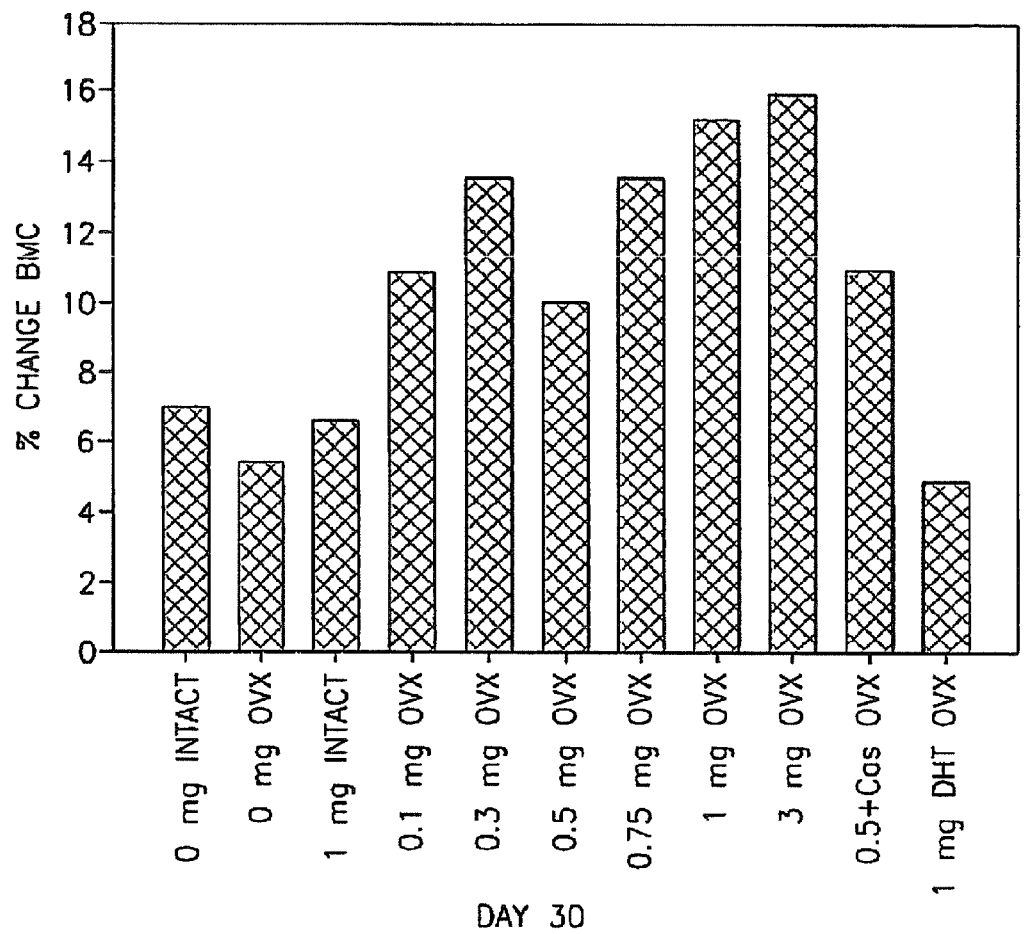
FIG. 8: Effect of SARMS on Bone Mineral Content (BMC) and Bone Mineral Density (BMD) in female rates after ovariectomy.
Figures 9A, 9B:
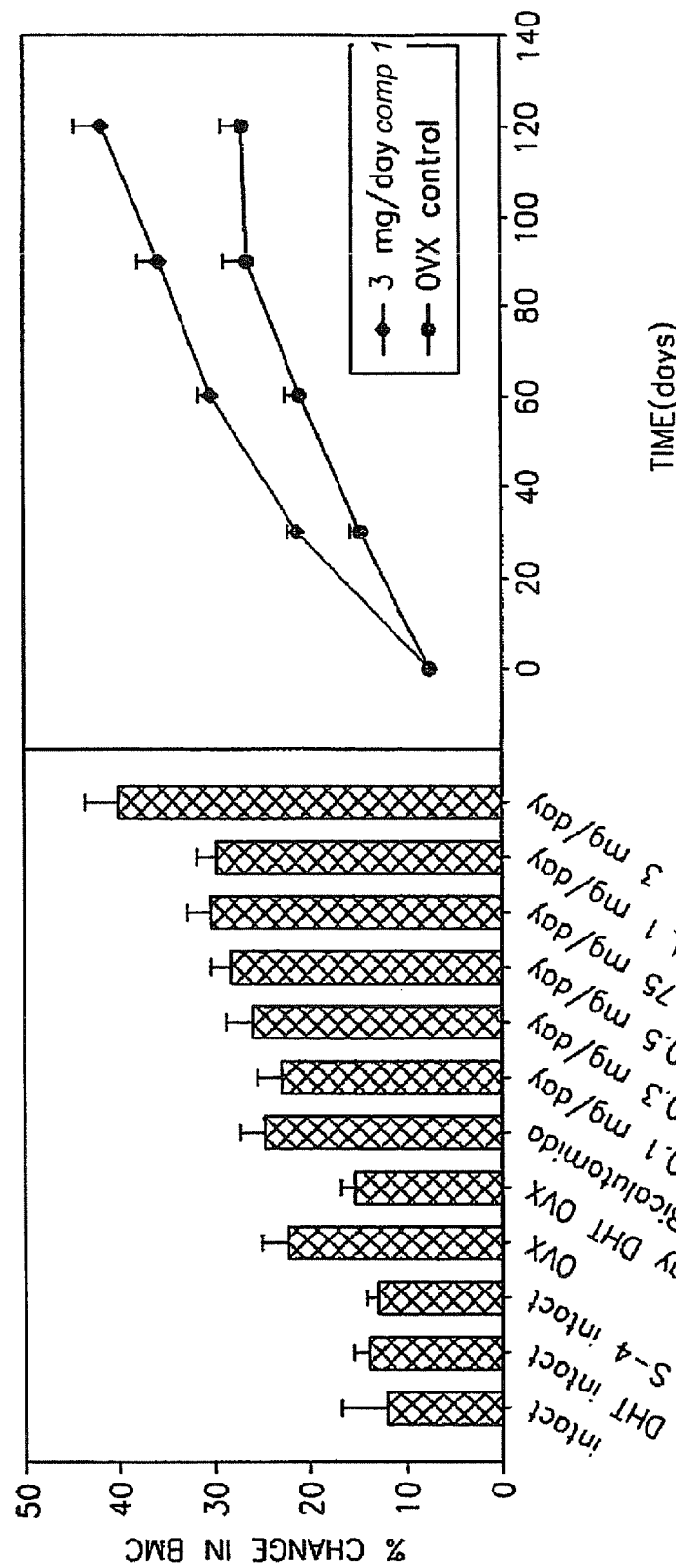
FIG. 9: Left panel: Compound 1 increased whole body BMC after 120 days. Right panel: time course of BMC changes in response to 3 milligrams/day Compound 1 treatment.

After 30 days of treatment, increases in BMC were observed in Compound 1, but not DHT, treated groups (FIG. 8). As shown in FIG. 9, Compound 1 increased whole body BMC in a dose-dependent and time-dependent manner, with increases of 22.9, 26.0, 28.5, 30.5, 30.0, and 40.1%, observed in groups 7-12, respectively, after 120 days (left panel), in a time-dependent fashion (right panel). By contrast, DHT increased BMC by 15%. The anti-androgen bicalutamide inhibited the effect of Compound 1 in this model, indicating drug effects were mediated through the AR. Thus, Compound 1 was more potent than DHT in inhibiting bone resorption.

Figure 10A:
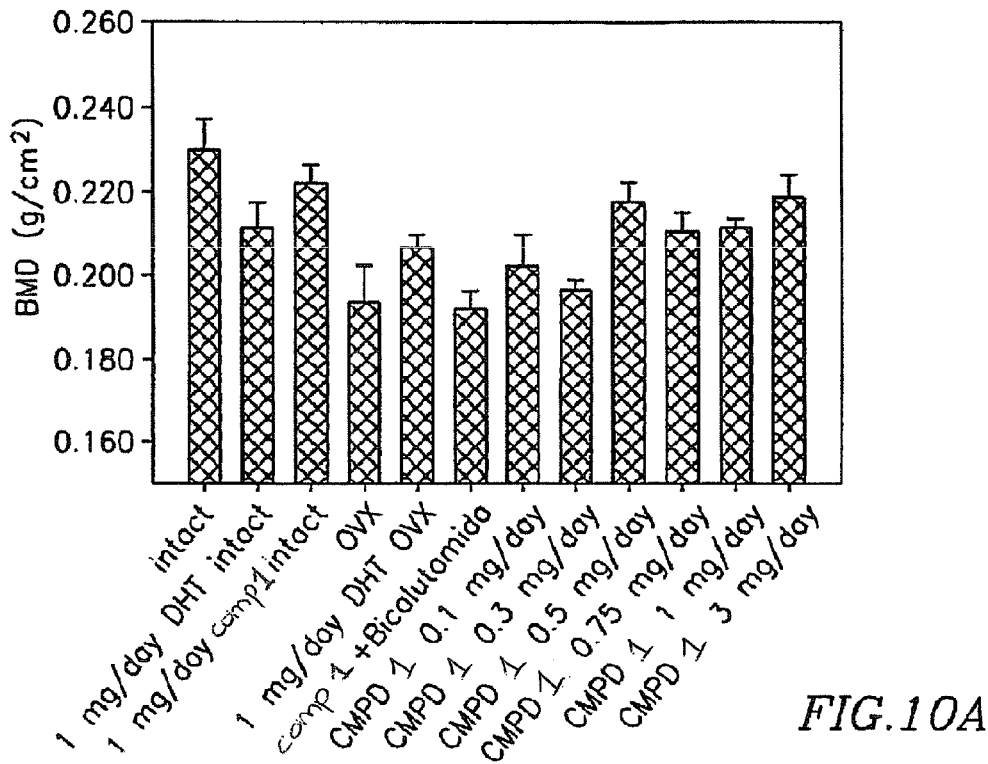
FIG. 10: Compound 1 exerted a protective effect at both the L2-L4 vertebra (up) and proximal femur (down).
Figure 10B:
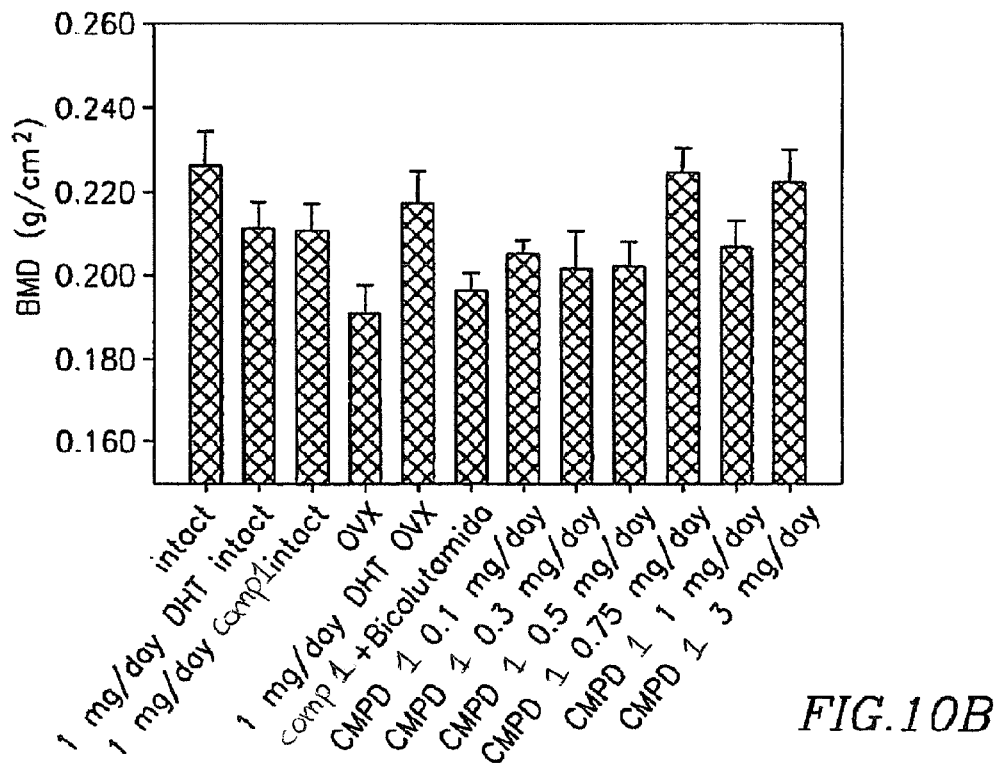

As shown in FIG. 10, Compound 1 prevented bone resorption at both the L2-L4 vertebra (left panel) and the proximal femur (right panel). Bicalutamide abrogated the protective effect of Compound VI at both sites.

Biomechanical Strength

Figure 11A:
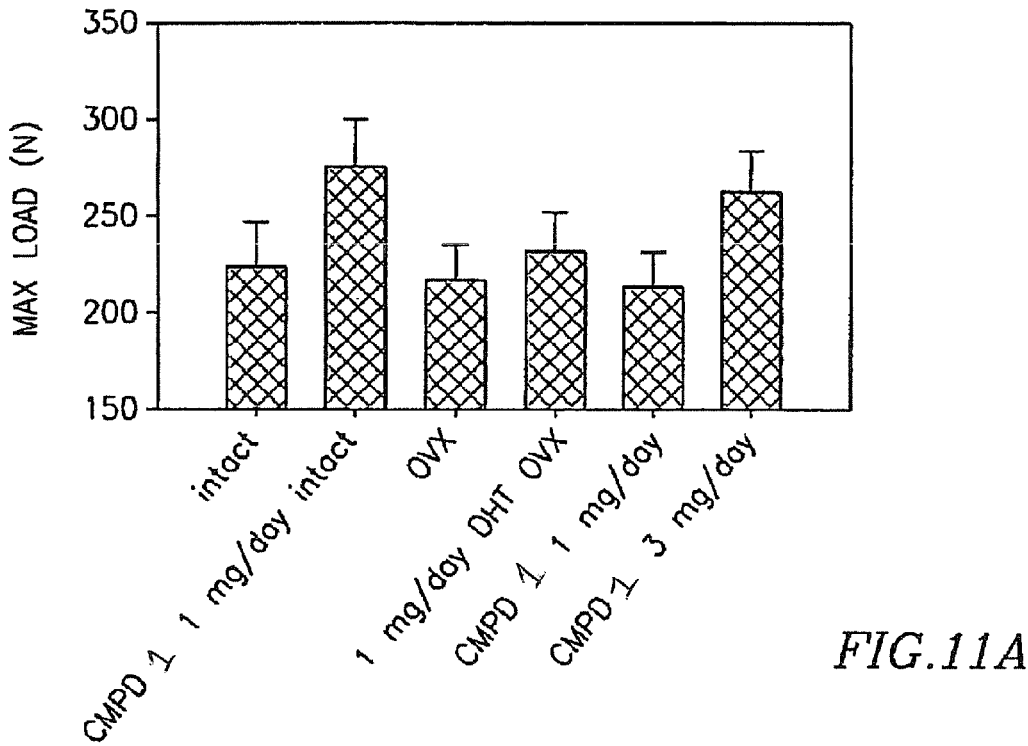
FIG. 11: Compound 1 increased biomechanical strength of the L5 vertebra (up) and femur (down).
Figure 11B:
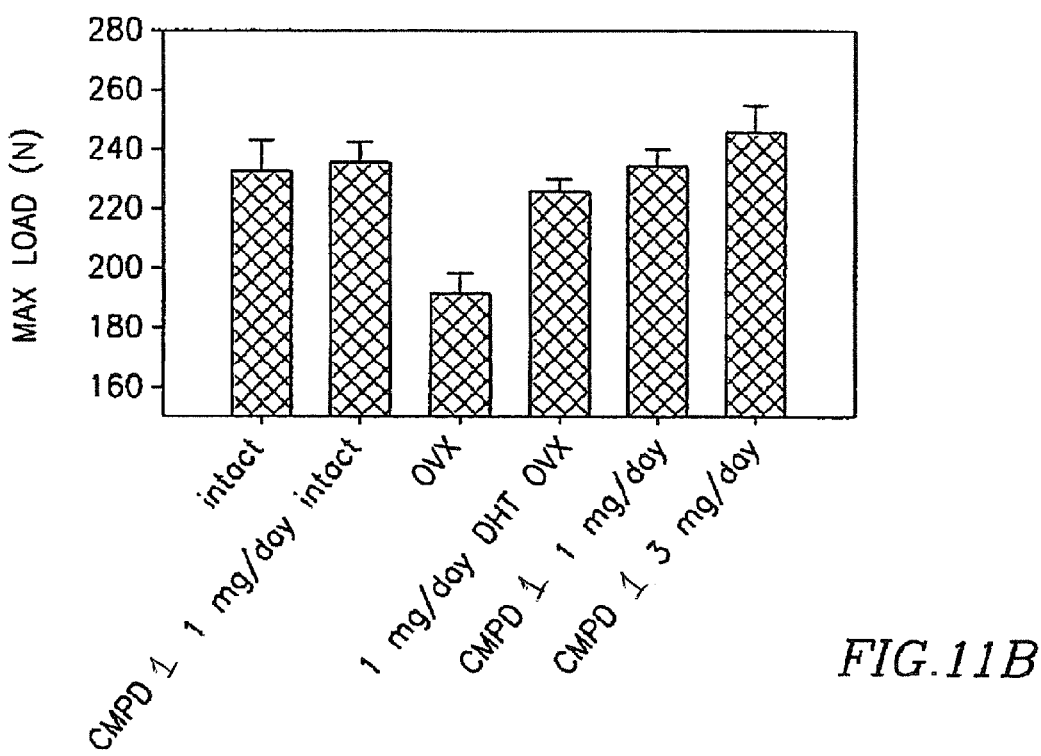

As shown in FIG. 11, Compound 1 increased biomechanical strength of the L5 vertebra (left panel) and femur (right panel). Since cortical bone is largely responsible for the strength of skeletal bone, these results demonstrate that Compound 1 prevented resorption of cortical bone.

Figure 12A:
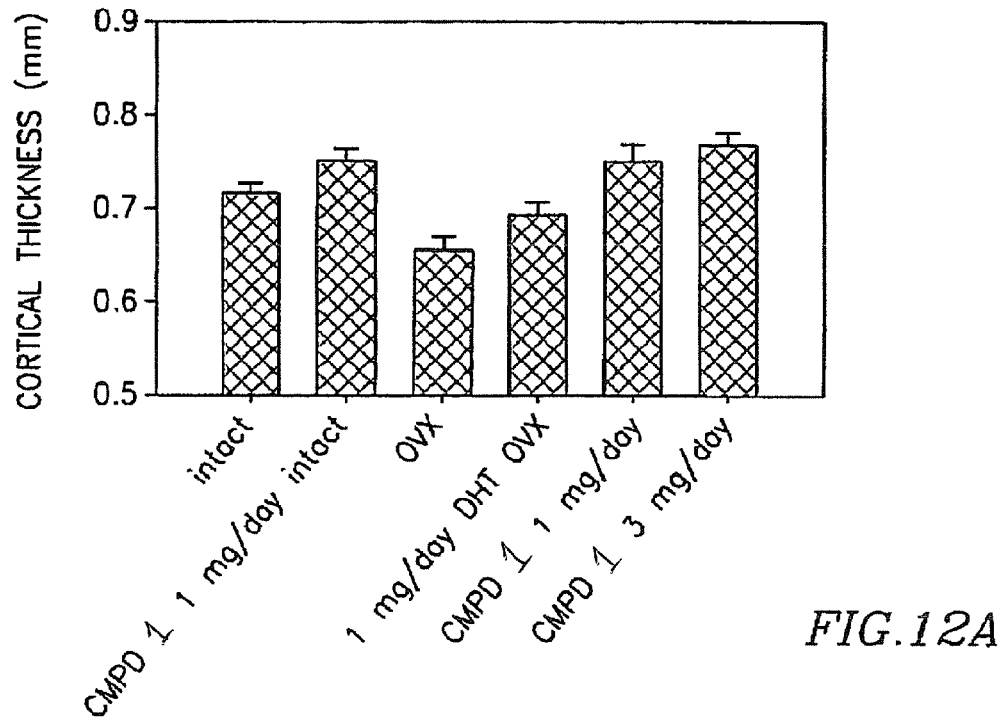
FIG. 12: Compound 1 increased cortical thickness (up) and trabecular density (down) in the femoral mid-shaft.
Figure 12B:
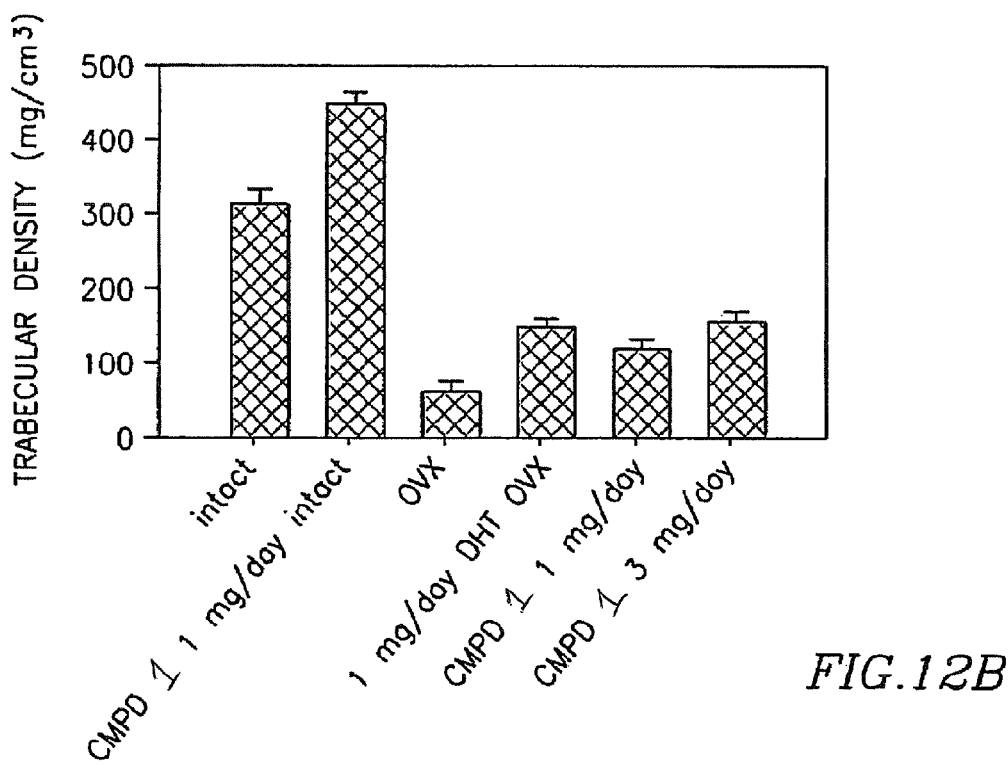
Figure 13:
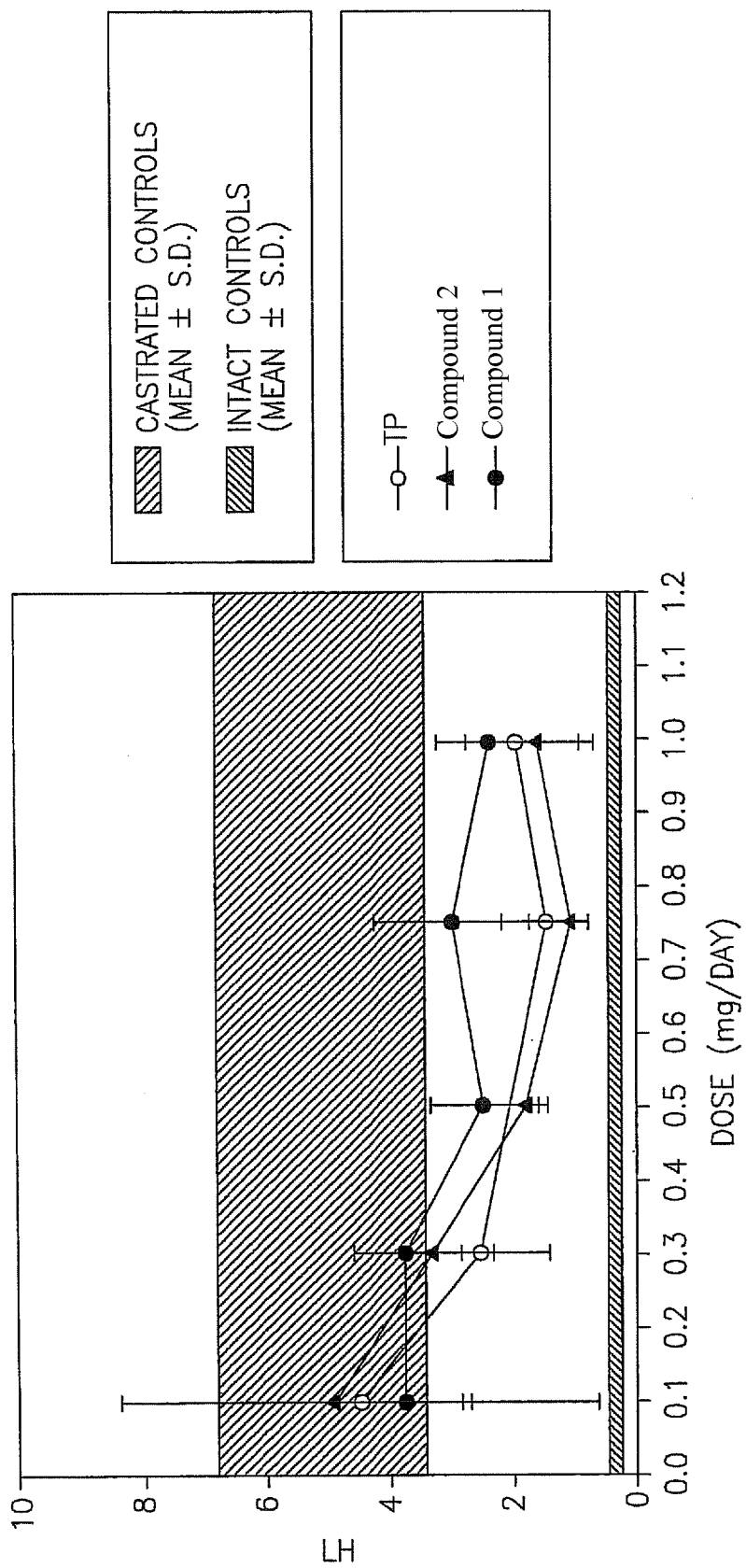
FIG. 13: Effects of Compound 1 and Compound 2 on LH Levels.
Figure 14:
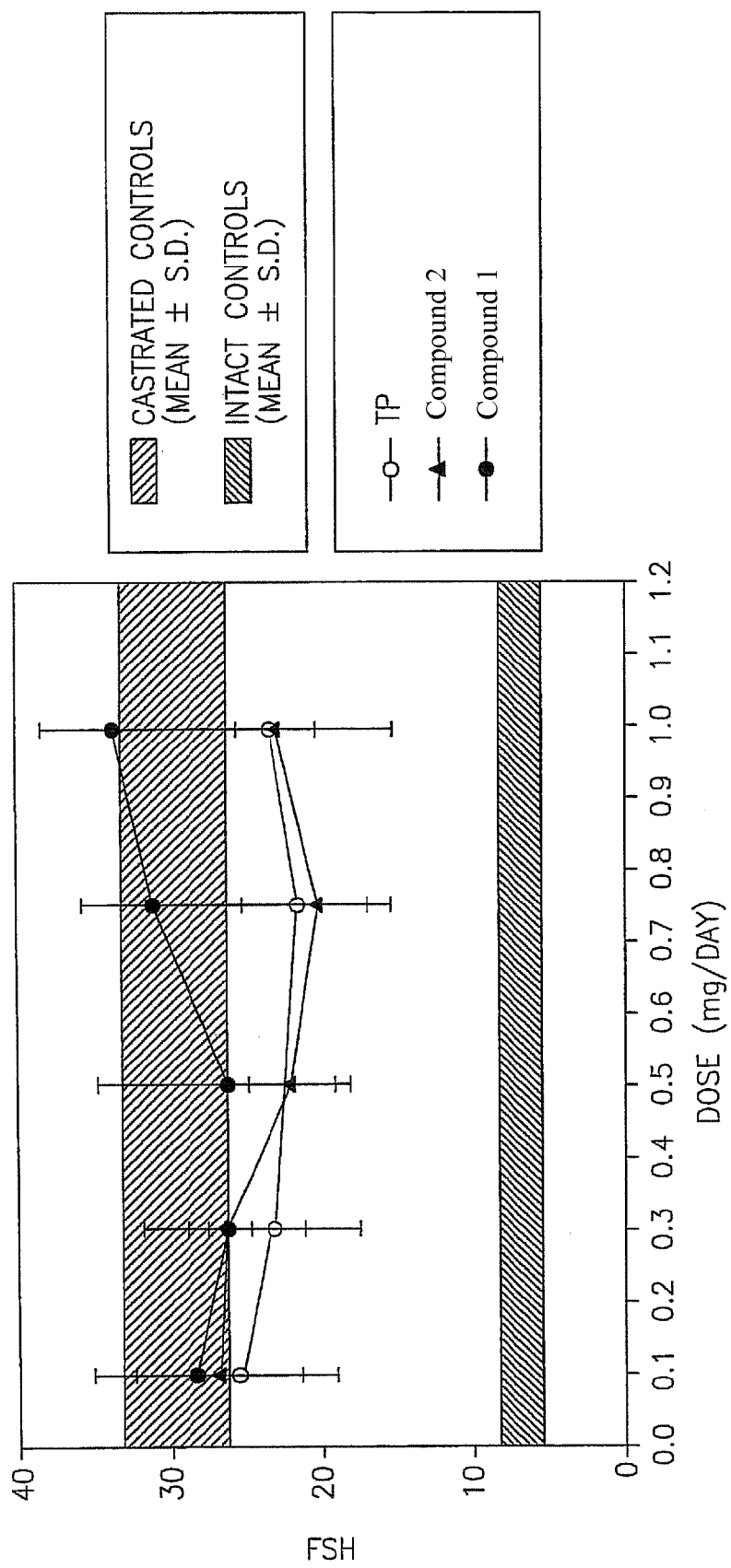
FIG. 14: Effects of Compound 1 and Compound 2 on FSH Levels.
Figure 15:
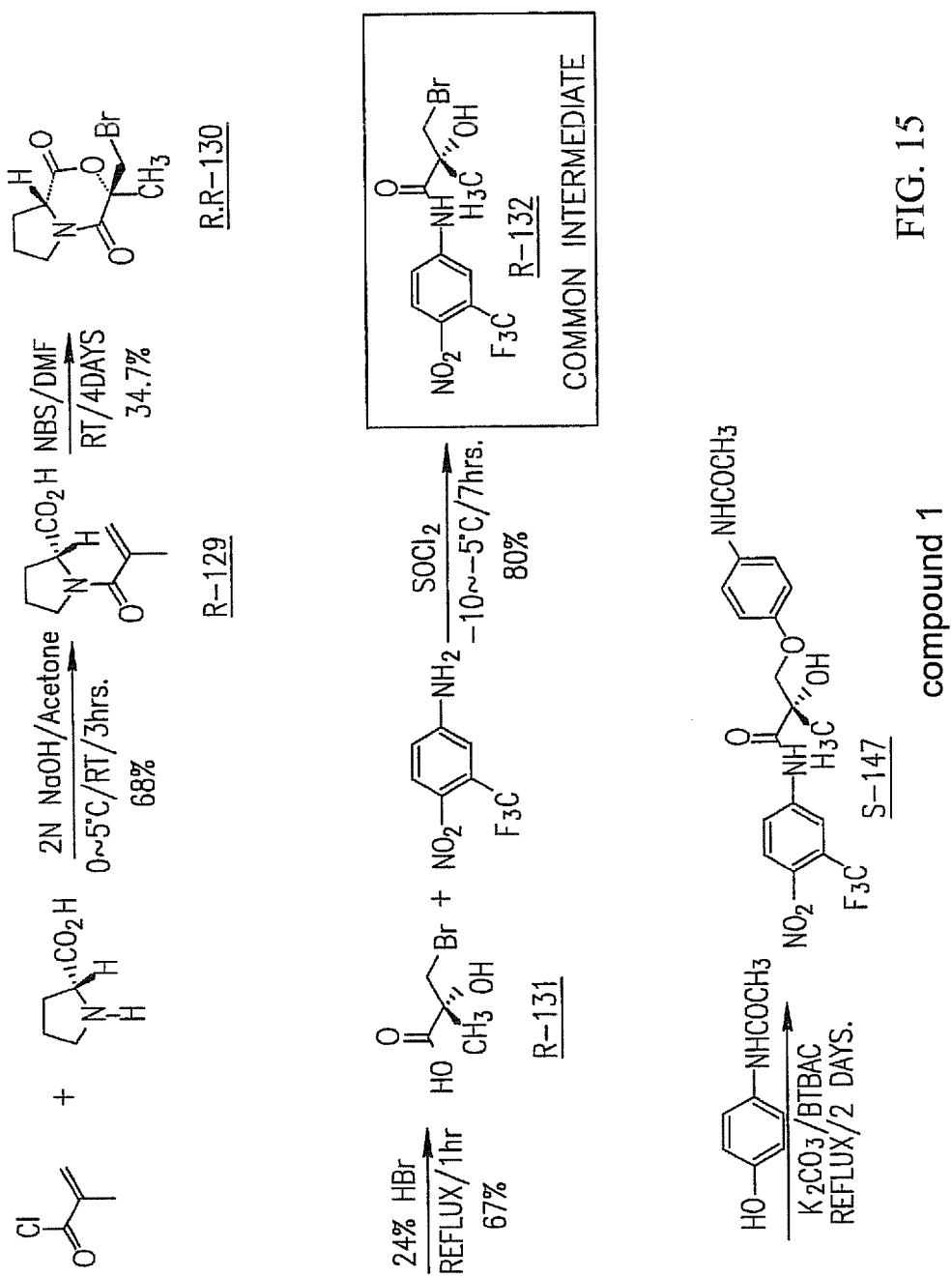
FIG. 15: Synthesis scheme of Compound 1.
Figure 16A:
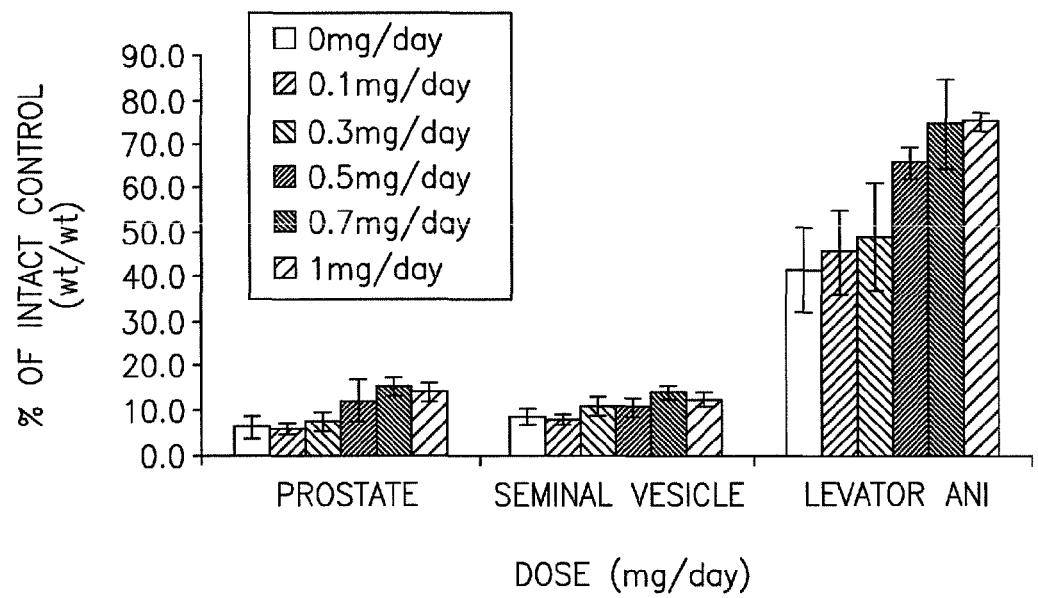
FIG. 16: Androgenic and Anabolic activity of Compounds 2-5. Rats were left untreated (intact control), castrated (0 mg/day control), or treated with 0.1, 0.3, 0.5, 0.75 and 1.0 mg/day of compound 2 (FIG. 1A), compound 3 (FIG. 1B), compound 4 (FIG. 1C) or compound 5 (FIG. 1D), and the weight of androgen-responsive tissues (prostate, semimal vesicles and levator ani muscle) was determined.
Figure 16B:
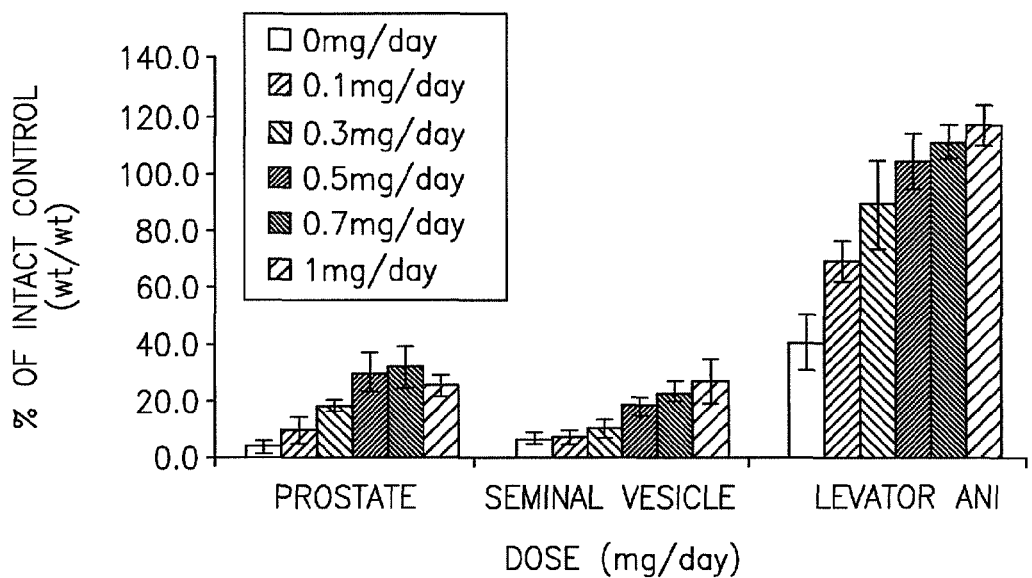
Figure 16C:
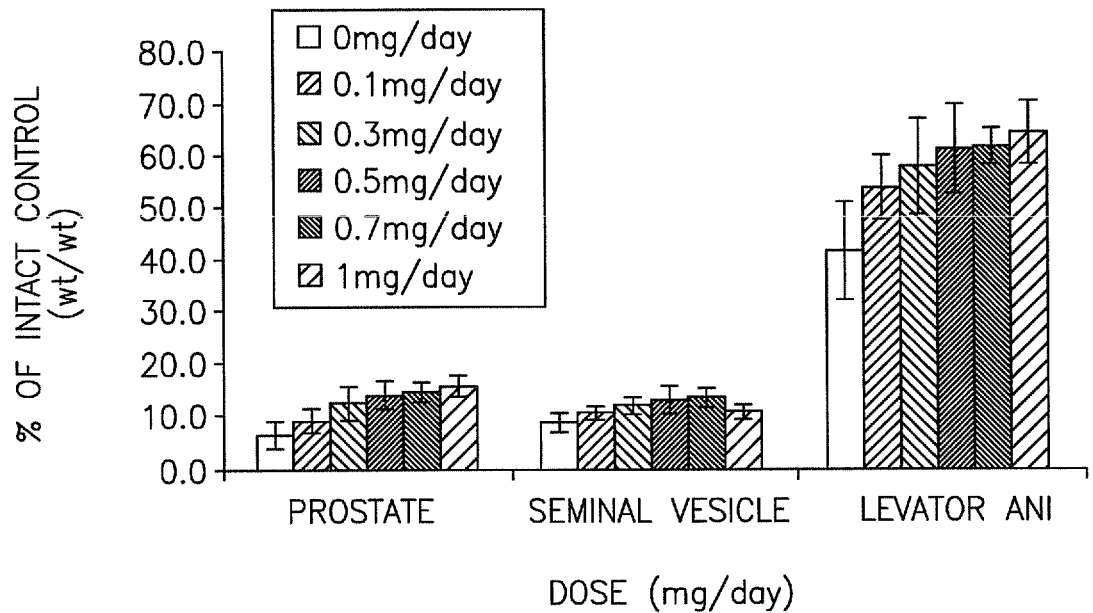
Figure 16D:
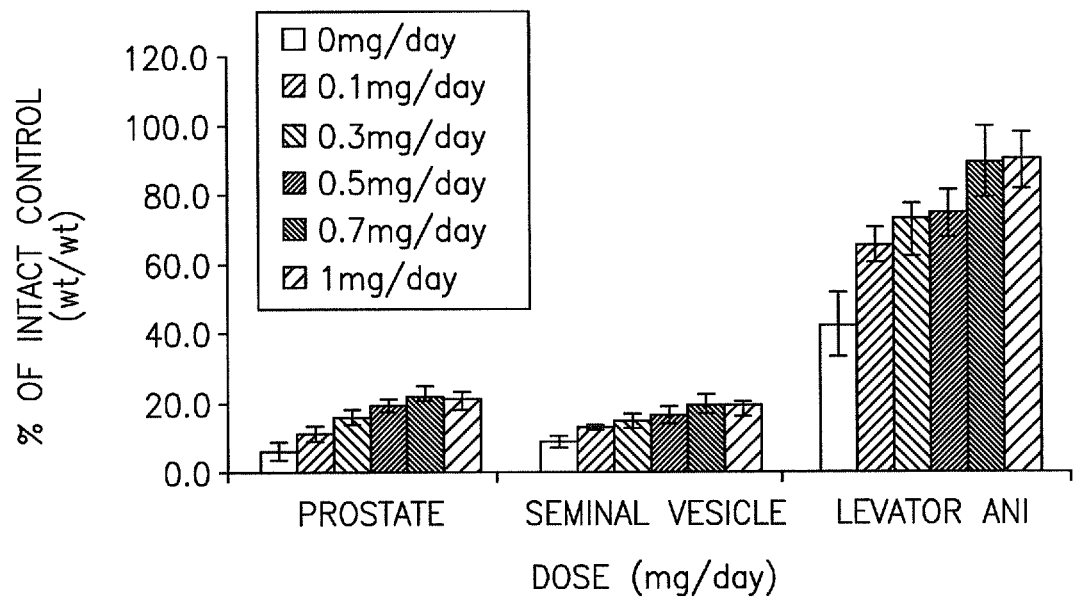

Effects on cortical and trabecular bone. As shown in FIG. 12, left panel, Compound 1 increased cortical thickness in the femoral mid-shaft relative to untreated ovarectomized animals, providing further evidence that Compound 1 prevented resorption of cortical bone. In addition, Compound 1 partially prevented resorption of trabecular bone, as evidenced by increased trabecular bone density in the distal femur (FIG. 12, right panel). In summary, the finding of this Example show that SARM compounds prevent resorption of both cortical and trabecular bone. The use of multiple assays and multiple bone locations to demonstrate this finding shows that SARM compounds improve multiple aspects of bone, such as bone mass, bone quality, and biomechanical strength, and demonstrates that the improvement of bone by SARM compounds is manifest in many locations throughout the body.

TABLE 5

Comparison of androgenic and anabolic effects of Compound 1 and TP on intact, hemi-orchidectomized and castrated rats (% of intact control, n = 5).

| Organs | | Control | Compound 1 | TP |
|---|---|---|---|---|
| Prostate | Intact | 100.00 ± 13.13 | 79.41 ± 9.32*† | 97.45 ± 10.82 |
| | Hemi-Castrated | 86.42 ± 19.52 | 74.69 ± 8.44*† | 98.57 ± 7.98 |
| | | 7.19 ± 1.25 | 32.55 ± 11.65*†‡ | 76.78 ± 10.43*‡ |
| Seminal | Intact | 100.00 ± 18.84 | 90.54 ± 12.10 | 103.95 ± 13.23 |
| Vesicle | Hemi-Castrated | 102.93 ± 7.47 | 78.55 ± 13.58†‡ | 114.19 ± 23.81 |
| | | 8.97 ± 1.23 | 16.47 ± 5.21*†‡ | 63.48 ± 17.05*‡ |
| Levator Ani | Intact | 100.00 ± 12.69 | 109.15 ± 14.68 | 95.61 ± 9.34 |
| | Hemi-Castrated | 92.94 ± 7.83 | 108.10 ± 8.92‡ | 98.63 ± 10.47 |
| | | 42.74 ± 5.22 | 100.65 ± 10.86‡ | 87.27 ± 10.25‡ |

*$p < 0.05$ compared to intact control group.
†$p < 0.05$ compared to TP of same surgical status (i.e., intact, hemi-orchidectomized, or castrate).
‡$p < 0.05$ compared to control group of same surgical status.

Example 4

Androgenic and Anabolic Activity of Compounds 2-5

Animals. Immature male Sprague-Dawley rats, weighing 90 to 100 g, were purchased from Harlan Biosciences (Indianapolis, Ind.). The animals were maintained on a 12-hour light-dark cycle with food and water available ad libitum. The animal protocol was reviewed and approved by the Institutional Laboratory Animal Care and Use Committee.

Study Design. Rats were randomly distributed into treatment groups groups. One day prior to the start of drug treatment, animals were individually removed from the cage, weighed and anesthetized with an intraperitoneal dose of ketamine/xylazine (87/13 mg/kg; approximately 1 mL per kg). When appropriately anesthetized (i.e., no response to toe pinch), the animals' ears were marked for identification purposes. Animals were then placed on a sterile pad and their abdomen and scrotum washed with betadine and 70% alcohol. The testes were removed via a midline scrotal incision, with sterile suture being used to ligate supra-testicular tissue prior to surgical removal of each testis. The surgical wound site was closed with sterile stainless steel wound clips, and the site cleaned with betadine. The animals were allowed to recover on a sterile pad (until able to stand) and then returned to their cage.

Twenty-four hours later, animals were re-anesthetized with ketamine/xylazine, and an Alzet osmotic pump(s) (model 2002) was placed subcutaneouly in the scapular region. In this instance, the scapular region was shaved and cleaned (betadine and alcohol) and a small incision (1 cm) made using a sterile scalpel. The osmotic pump was inserted and the wound closed with a sterile stainless steel wound clip. Animals were allowed to recover and were returned to their cage. Osmotic pumps contained the appropriate treatment dissolved in polyethylene glycol 300 (PEG300). Osmotic pumps were filled with the appropriate solution one day prior to implantation. Animals were monitored daily for signs of acute toxicity to drug treatment (e.g., lethargy, rough coat).

After 14 days of drug treatment, rats were anesthetized with ketamine/xylazine. Animals were then sacrificed by exsanguinations under anesthesia. A blood sample was collected by venipuncture of the abdominal aorta, and submitted for complete blood cell analysis. A portion of the blood was placed in a separate tube, centrifuged at 12,000 g for 1 minute, and the plasma layer removed and frozen at −20° C. The ventral prostates, seminal vesicles, levator ani muscle, liver, kidneys, spleen, lungs, and heart were removed, cleared of extraneous tissue, weighed, and placed in vials containing 10% neutral buffered formalin. Preserved tissues were sent to GTx, Inc. for histopathological analysis.

For data analysis, the weights of all organs were normalized to body weight, and analyzed for any statistical significant difference by single-factor ANOVA. The weights of prostate and seminal vesicle were used as indexes for evaluation of androgenic activity, and the levator ani muscle weight was used to evaluate the anabolic activity.

Results

The androgenic and anabolic activities of compounds 2-5 were examined in a castrated rat model after 14 days of administration. The results are shown in FIG. 16 A-D as a percent of the Intact Contol (not castrated, untreated). 0 mg/day denotes Castrated Controls (castrated, untreated).

As shown in FIG. 16, the weights of prostate, seminal vesicle, and levator ani muscle in castrated rats decreased significantly, due to the ablation of endogenous androgen production. Treatment with increasing dosages of compounds 2-5 (FIG. 16A-D respectively) resulted in a tissue-selective increase in levator ani muscle weights, with little or no stimulation of prostate and seminal vesicle growth (i.e. the prostate and seminal vesicle weights were less than 40% of that observed in intact animals for compound 3, and less than 20% for compounds 2, 4 and 5). Thus these compounds showed little potency and intrinsic activity in increasing the weights of prostate and seminal vesicle, but a great potency and intrinsic activity in increasing the weight of levator ani muscle. Particularly, compound 3 was able to maintain the levator ani muscle weight of castrated animals in the same level as that of intact animals. Thus, compounds 2-5 are potent nonsteroidal anabolic agents. This is a significant improvement over previous compounds, in that these compound selectively stimulate muscle growth and other anabolic effects while having less effect on the prostate and seminal vesicles. This may be particularly relevant in aging men with concerns related to the development or progression of prostate cancer.

Example 5

Androgenic and Anabolic Activity of Compound 6

The binding affinity of compound 5 is represented in Table 6:

TABLE 6

| Name | Structure | MW | Ki |
|---|---|---|---|
| 6 | NC-, CF₃-, NH-C(=O)-C(CH₃)(OH)-CH₂-O-C₆H₄-F | 382.3 | 3.3 ± 0.08 |

The androgenic and anabolic activities of compound 6 were examined in a castrated rat model after 14 days of administration, using the method outlined in Example 4 above.

Figure 17:
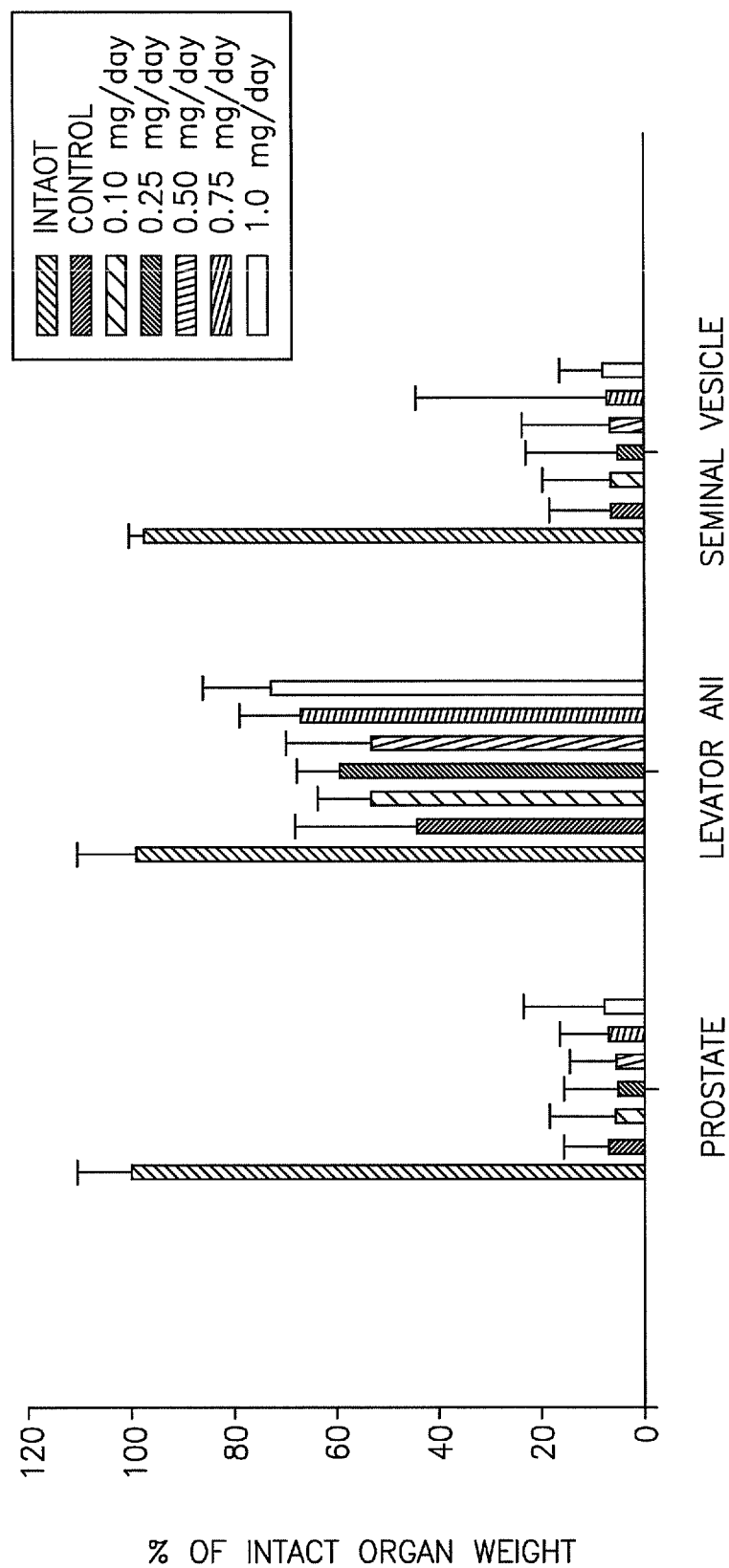
FIG. 17: Androgenic and Anabolic activity of Compound 6. Rats were left untreated (intact control), castrated (0 mg/day control), or treated with 0.1, 0.25, 0.5, 0.75 and 1.0 mg/day of compound 6, and the weight of androgen-responsive tissues (prostate, semimal vesicles and levator ani muscle) was determined.

As shown in Table 7 and in FIG. 17, compound 6 demonstrated tissue-selective pharmacological effects in castrated male rats, with higher efficacy in anabolic tissues (i.e. levator ani) as compared to androgenic tissues (i.e. prostate and seminal vesicles). Compound 6 demonstrated little pharmacologic activity in the prostate (8.7±1.39% of intact at 1.0 mg/day dose) and sminal vesicles (10.7±0.91% of intact at 1.0 mg/day dose), suggesting that it acts as a weak partial agonist in these tissues. Importantly, compound 6 demonstrates highly efficacious anabolic activity at 1.0 mg/day dose, returning the levator ani muscle to 75.2±9.51% of that observed in intact animals.

TABLE 7

| | Average (Mean ± S.D.) Organ Weights | | |
|---|---|---|---|
| | Prostate | Levator Ani | Seminal Vesicles |
| Intact Control | 100 ± 11.28 | 100 ± 12.12 | 100 ± 2.48 |
| Castrated Control | 7.6 ± 0.68 | 45.9 ± 10.84 | 8.4 ± 1.05 |
| 0.10 mg/day | 6.4 ± 0.82 | 54.9 ± 5.77 | 8.8 ± 1.18 |
| 0.25 mg/day | 5.7 ± 0.61 | 61.0 ± 5.23 | 7.6 ± 1.37 |
| 0.50 mg/day | 6.2 ± 0.56 | 55.0 ± 9.23 | 9.3 ± 1.57 |
| 0.75 mg/day | 7.6 ± 0.74 | 68.9 ± 8.46 | 9.8 ± 3.65 |
| 1.00 mg/day | 8.7 ± 1.39 | 75.2 ± 9.51 | 10.7 ± 0.91 |

Example 6

Androgenic and Anabolic Activity of Compound 7

The binding affinitiy of select compound 7 is represented in Table 8:

TABLE 8

| Name | Structure | MW | Ki |
|---|---|---|---|
| 7 | NC-, CF₃-, NH-C(=O)-C(CH₃)(OH)-CH₂-O-C₆H₄-Cl | 398.8 | 3.4 ± 0.08 |

The androgenic and anabolic activities of compound 7 was examined in a castrated rat model after 14 days of administration, using the method outlined in Example 4 above.

Figure 18:
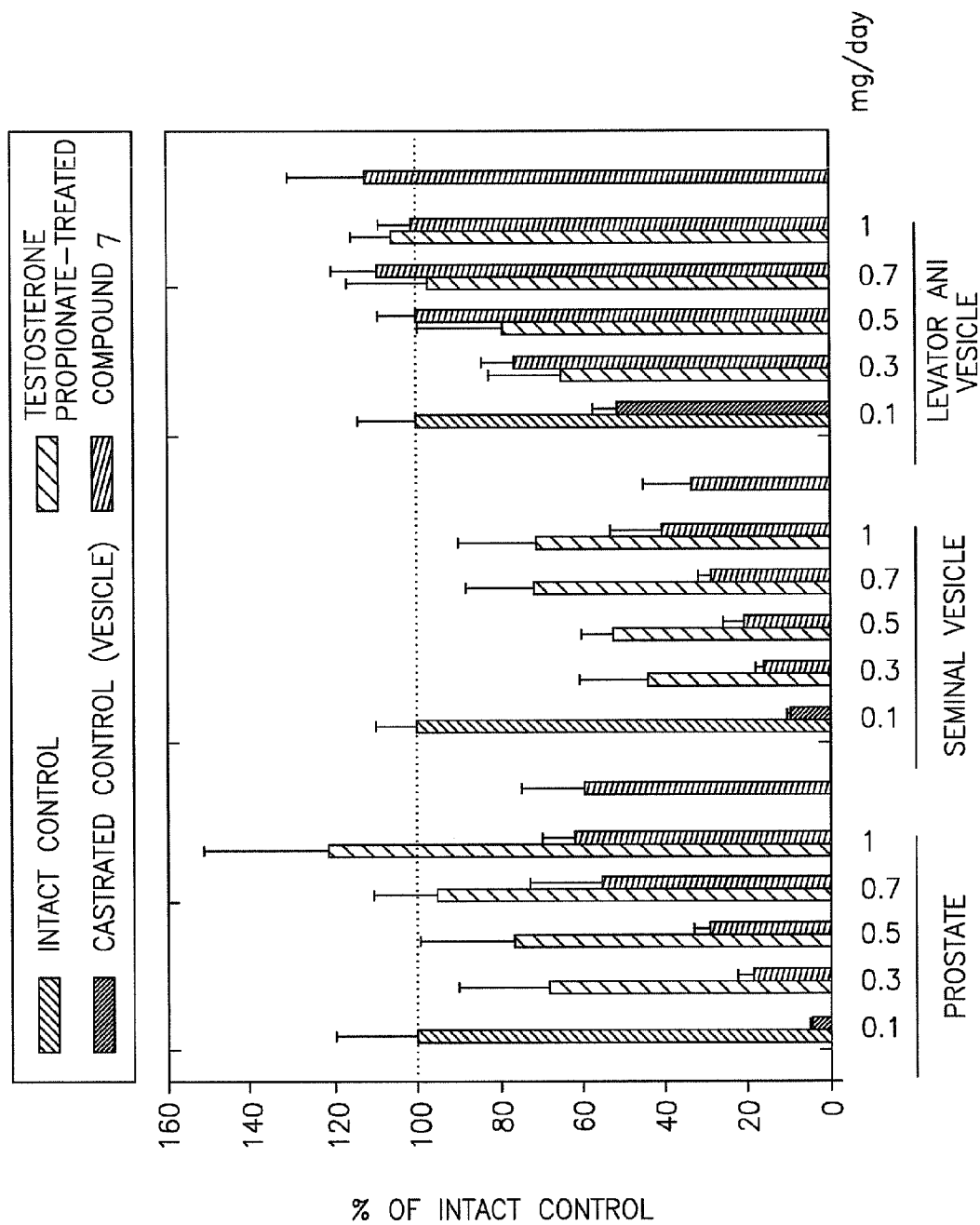
FIG. 18: Androgenic and Anabolic activity of Compound 7 in rats. Rats were left untreated (intact control), castrated (castrated control), treated with 0.1, 0.3, 0.5, 0.75 and 1.0 mg/day testosterone propionate (TP), or treated with 0.1, 0.3, 0.5, 0.75 and 1.0 mg/day Compound 7, and the weight of androgen-responsive tissues (prostate, semimal vesicles and levator ani muscle) was determined.

As shown in FIG. 18, the weights of prostate, seminal vesicle, and levator ani muscle in castrated, vehicle-treated rats decreased significantly, due to the ablation of endogenous androgen production. Exogenous administration of testosterone propionate, an androgenic and anabolic steroid, increased the weights of prostate, seminal vesicle, and levator ani muscle in castrated rats in a dose-dependent manner. Treatment with compound 7 resulted in dose-dependent increases in prostate, seminal vesicle and levator ani muscle weights. Compared with testosterone propionate, compound 7 showed lower potency and intrinsic activity in increasing the weights of prostate and seminal vesicle, but a greater potency and intrinsic activity in increasing the weight of levator ani muscle. Particularly, compound 7, at a dose as low as 0.3 mg/day, was able to maintain the levator ani muscle weight of castrated animals in the same level as that of intact animals. Thus, compound 7 is a potent nonsteroidal anabolic agent with less androgenic activity but more anabolic activity than testosterone propionate. As in compounds 2-6 above, this is a significant improvement in that this compound selectively stimulates muscle growth and other anabolic effects while having less effect on the prostate and seminal vesicles.

In summary, the findings of the present invention demonstrate that SARM compounds (1) are anabolic in bone (both cortical and trabecular) and muscle in testosterone-depleted subjects, and subjects with slight androgen depletion; (2) have no effects on testosterone, FSH, or LH levels; (3) exhibit mixed AR agonist activity in sexual accessory glands; and (4) prevent bone resorption in testosterone-depleted subjects. The findings also demonstrate that the type and quantity of AR activity, and the tissues most effective, vary between different SARM compounds.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating a male subject suffering from an Androgen Decline in Aging Male (ADAM)-associated condition, wherein said ADAM-associated condition is selected from the group consisting of fatigue, depression, decreased libido, sexual dysfunction, erectile dysfunction, hypogonadism, osteoporosis, hair loss, anemia, obesity, sarcopenia, osteopenia, benign prostate hyperplasia, alterations in mood and cognition and prostate cancer, said method comprising the step of administering to said subject a selective androgen receptor modulator (SARM) compound represented by the structure of formula I:

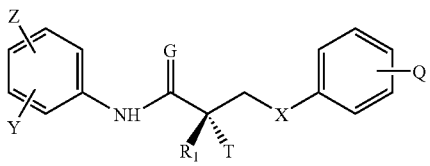

I wherein G is O or S;
X is O;
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
Q is alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, OCN;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH; and
R$_1$ is CH$_3$, CH$_2$F, CHF$_2$, CF$_3$, CH$_2$CH$_3$, or CF$_2$CF$_3$;
or its optical isomer or pharmaceutically acceptable salt, or any combination thereof.

2. The method according to claim 1, wherein said SARM compound is represented by the structure of formula II:

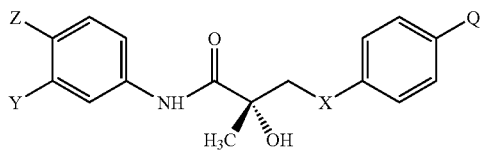

II wherein X is O;
Z is NO$_2$, CN, COOH, COR, NHCOR or CONHR;
Y is CF$_3$, F, I, Br, Cl, CN, C(R)$_3$ or Sn(R)$_3$;
Q is alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, OCN;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH.

3. The method of claim 1, wherein said Z is CN.
4. The method of claim 1, wherein said Q is halogen.
5. The method according to claim 1, wherein said SARM compound is represented by the structure of formula 6:

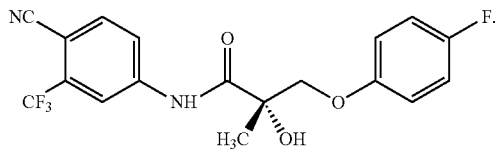

6. The method of claim 1, wherein said SARM does not penetrate the central nervous system (CNS).
7. The method of claim 1, further comprising administering a pharmaceutical preparation comprising said SARM compound and/or its optical isomer or pharmaceutically acceptable salt or any combination thereof; and a pharmaceutically acceptable carrier.
8. The method according to claim 7, comprising intravenously, intraarterially, or intramuscularly injecting to said subject said pharmaceutical preparation in liquid form; subcutaneously implanting in said subject a pellet containing said pharmaceutical preparation; orally administering to said subject said pharmaceutical preparation in a liquid or solid form; or topically applying to the skin surface of said subject said pharmaceutical preparation.
9. The method according to claim 7, wherein said pharmaceutical preparation is a pellet, a tablet, a capsule, a solution, a suspension, an emulsion, an elixir, a gel, a cream, a suppository or a parenteral formulation.
10. The method of claim 1, wherein said male subject is an aging male subject.
11. A method of suppressing, inhibiting or reducing the incidence of an Androgen Decline in Aging Male (ADAM)-associated condition in a male subject, wherein said ADAM-associated condition is selected from the group consisting of fatigue, depression, decreased libido, sexual dysfunction, erectile dysfunction, hypogonadism, osteoporosis, hair loss, anemia, obesity, sarcopenia, osteopenia, benign prostate hyperplasia, alterations in mood and cognition and prostate cancer, said method comprising the step of administering to said subject a selective androgen receptor modulator (SARM) compound represented by the structure of formula I:

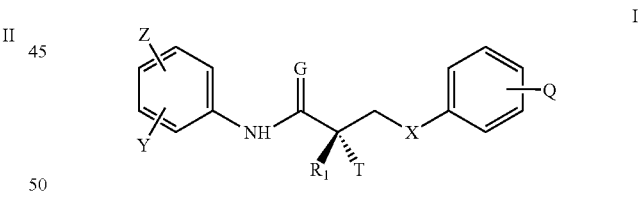

I wherein G is O or S;
X is O;
T is OH, OR, —NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
Q is alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, OCN;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH; and
R$_1$ is CH$_3$, CH$_2$F, CHF$_2$, CF$_3$, CH$_2$CH$_3$, or CF$_2$CF$_3$;
or its optical isomer or pharmaceutically acceptable salt, or any combination thereof.

12. The method according to claim 11, wherein said SARM compound is represented by the structure of formula II;

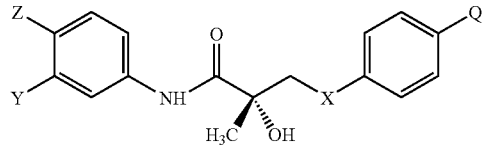

wherein X is O;

Z is NO$_2$, CN, COOH, COR, NHCOR or CONHR;

Y is CF$_3$, F, I, Br, Cl, CN, C(R)$_3$ or Sn(R)$_3$;

Q is alkyl, F, Cl, Br, I, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO, OCN;

R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH.

13. The method of claim 11, wherein said Z is CN.

14. The method of claim 11, wherein said Q is halogen.

15. The method according to claim 11, wherein said SARM compound is represented by the structure of formula 6:

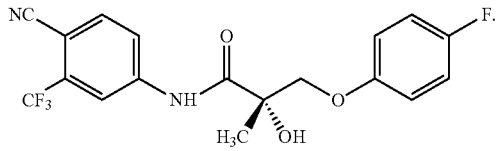

16. The method of claim 11, wherein said SARM does not penetrate the central nervous system (CNS).

17. The method of claim 11, further comprising administering a pharmaceutical preparation comprising said SARM compound and/or its optical isomer or pharmaceutically acceptable salt, or any combination thereof; and a pharmaceutically acceptable carrier.

18. The method according to claim 17, comprising intravenously, intraarterially, or intramuscularly injecting to said subject said pharmaceutical preparation in liquid form; subcutaneously implanting in said subject a pellet containing said pharmaceutical preparation; orally administering to said subject said pharmaceutical preparation in a liquid or solid form; or topically applying to the skin surface of said subject said pharmaceutical preparation.

19. The method according to claim 17, wherein said pharmaceutical preparation is a pellet, a tablet, a capsule, a solution, a suspension, an emulsion, an elixir, a gel, or a cream.

20. The method of claim 11, wherein said male subject is an aging male subject.

* * * * *